(12) United States Patent
Sowers et al.

(10) Patent No.: US 6,946,248 B2
(45) Date of Patent: Sep. 20, 2005

(54) COMPOSITIONS AND METHODS FOR MICROBIAL DECHLORINATION OF POLYCHLORINATED BIPHENYL COMPOUNDS

(75) Inventors: Kevin R. Sowers, Baltimore, MD (US); Harold D. May, Charleston, SC (US)

(73) Assignees: University of Maryland, Baltimore, MD (US); Biotechnology Institute Medical University of South Carolina, Charleston, SC (US)

( * ) Notice: Subject to any disclaimer, the term of this patent is extended or adjusted under 35 U.S.C. 154(b) by 0 days.

(21) Appl. No.: 09/860,200

(22) Filed: May 18, 2001

(65) Prior Publication Data

US 2003/0134408 A1 Jul. 17, 2003

Related U.S. Application Data

(60) Provisional application No. 60/205,818, filed on May 19, 2000, now abandoned, and provisional application No. 60/266,650, filed on Feb. 6, 2001.

(51) Int. Cl.$^7$ .............................. C12Q 1/68; C12N 1/00; B09B 3/00

(52) U.S. Cl. .......................... 435/6; 435/243; 435/262.5

(58) Field of Search ............................... 435/243, 262.5, 435/6, 7.1, 91.1, 91.2; 530/22.1, 23.1, 24.3–24.33

(56) References Cited

U.S. PATENT DOCUMENTS

| | | | |
|---|---|---|---|
| 3,779,866 A | 12/1973 | Azarowicz | 195/2 |
| 4,843,007 A | 6/1989 | Bedard et al. | 435/252.1 |
| 4,876,201 A | 10/1989 | Bedard et al. | 435/262 |
| 4,950,309 A | 8/1990 | Schulz | 48/197 R |
| 5,227,069 A | 7/1993 | Van Dort et al. | 210/610 |
| 5,242,601 A | 9/1993 | Manchak, Jr. et al. | 210/711 |
| 5,484,729 A | 1/1996 | DeWeerd et al. | 435/262.5 |
| 5,540,838 A | 7/1996 | Smullen et al. | 210/610 |
| 5,618,727 A | 4/1997 | Lajoie et al. | 435/262.5 |
| 5,635,393 A | 6/1997 | Bhatnagar et al. | 435/262.5 |
| 5,750,065 A | 5/1998 | Kilbane, II | 264/344 |
| 5,773,283 A | 6/1998 | Pierce | 435/262 |
| 5,834,222 A | 11/1998 | Friedman et al. | 435/793 |
| 5,858,692 A | 1/1999 | Friedman et al. | 435/7.93 |
| 5,932,472 A | 8/1999 | Abdullah | 435/262.5 |
| 5,968,360 A | 10/1999 | Crowley et al. | 210/611 |
| 6,797,817 B1 * | 9/2004 | Ebersole et al. | 536/24.3 |
| 6,894,156 B2 * | 5/2005 | Ebersole et al. | 536/24.1 |

OTHER PUBLICATIONS

Tracey R. Pullam Holoman, et al. "Characterization of a Defined 2,3,5,6–Tetrachlorobiphenyl–ortho–Declorinating Microbial Community Comparative Sequence Analysis of Genes Coding for 16S rRNA", Applied and Environmental Microbiology, pp. 3359–3367, Sep. 1998.

Drenzek et al., *The Absence and Application of Stable Carbon Isotopic Fractionation during the Reductive Dechlorination of Polychlorinated Biphenys*, Environ. Sci. & Technol., pp. A–D.

Abstract—Watts et al., *Comparative Analysis of PCB–Declorinating Communities in Enrichment Cultures Using Three Different Molecular Screening Techniques*, Environ. Microbiology.

Abstract—Wu et al., *Identification of a Bacterium That Specifically Catalyzes the Reductive Dechlorination of PCBs with Doubly Flanked Chlorines*.

Abstract—Cutter et al., *Identification of a Microrganism that Links its Growth to the Reductive Dechlorination of 2,3,5,6–Chlorobiphenyl*.

Ausubel et al., *Current Protocols in Molecular Biology*, Greene Publishing Associates, Inc. (1993), pp. 2.1–2.38; 3.1–3.44; 5.1–5.25 and 6.1–6.16.

Meinkoth, et al., Anal. Biochem. 138, 267–284 (1984).

Holoman, T.R.P., Elberson, M.A., Cutter, L., May, H.D., and Sowers, K. R., 1998, *Characterization of a defined 2,3,5, 6–tetrachlorobiphenyl ortho–dechlorinating microbial community by comparative sequence analysis of genes coding for 16S rDNA*, Appl. Environ. Microbiol., 64:3359–3367 (1998).

Presentation: Acetate–Dependent ortho PCB Dechlorination, Joint Meeting of the Southeastern Branches, American Society for Microbiology, Oct. 28–30, 1999, Jekyll Island, Georgia.

Berkaw, M., Sowers, K.R. and May, H.D., *Anaerobic ortho–dechlorination of polychlorinated biphenyls by estuarine sediments from Baltimore Harbor*, Appl. Environ. Microbiol., 62: 2534–2539 (1996).

Wu, Q., Sowers, K.R. and May, H.D., *Microbial reductive dechlorination of Aroclor 1260 in anaerobic slurries of estuarine sediments*, Appl. Environ. Microbiol. 64:1052–1058 (1998).

Cutter, L., Sowers, K.R. and May, H.D., *Microbial Dechlorination of 2,3,5,6–Tetrachlorobiphenyl under Anaerobic Conditions in the Absence of Soil or Sediment*, Appl. Environ. Microbiol., 64:2966–2969 (1998).

Clark et al., Applied and Environmental Microbiology, vol. 37, No. 4 (1979).

(Continued)

*Primary Examiner*—Kenneth R. Horlick
(74) *Attorney, Agent, or Firm*—Marianne Fuierer; Steven J. Hultquist

(57) ABSTRACT

Bioremediative microorganisms comprising a 16S ribosomal subunit nucleic acid sequence and useful in various methods for dechlorinating chlorinated biphenyls (PCBs), including anaerobic dechlorination of ortho- and double-flanked chloro substituents of PCBs. The methods of bioremediation may employ consortia of microbially effective species, e.g., aerobic as well as anaerobic species, to dechlorinate corresponding PCB mixtures containing widely varying and significant numbers of PCB congeners.

26 Claims, 30 Drawing Sheets

OTHER PUBLICATIONS

Bedard, D.L. and Quensen, III, J.F., *Microbial reductive dechlorination of polychlorinated biphenyls*, p. 127–216, in Young, L.Y. and Cerniglia, C. (eds.), Microbial Transformation and Degradation of Toxic Organic Chemicals, John Wiley & Sons, Inc., New York (1995).

Cole, J.R., Cascarelli, A.L., Mohn, W.W., and Tiedje, J.M., *Isolation and characterization of a novel bacterium growing via reductive dechlorination of 2–chlorophenol*, Appl. Environ. Microbiol., 60(10), 3536–3542 (1994).

DeWeerd, K.A., Concannon, F. and Suflita, J.M., *Relationship between hydrogen consumption, dehalogenation, and the reduction of sulfur oxyanions by Desulfomonile tiedjei*, Appl. Environ. Microbiol., 57 (7): 1929–1934 (1991).

Freedman, D.L., and Cossett, J.M., *Biological reductive dechlorination of tetrachloroethylene and trichloroethylene under methanogenic conditions*, Appl. Environ. Microbiol. 55:2144–2151 (1989).

May, H.D., Cutter, L.A., Watts, J.E.M. and Sowers, K.R, *Molecular Identification of an Anaerobic Microorganism Whose Growth is Linked to PCB Dechlorination*, presented at The 17$^{th}$ Annual International Conference on Contaminated Soils, Sediments and Water, Oct. 15–19, 2000, University of Massachusetts at Amherst.

Maymo–Gatell, X., Chien, Y.T., Gossett, J.M., and Zinder, S.H., *Isolation of a bacterium that reductively dechlorinates tetrachloroethene to ethane*, SCIENCE, 276:1568–1571 (1997).

Middledorp, P.J.M., DeWolf, A., Zehnder, J.B. and Schraa, G., *Enrichment and properties of a 1,2,4–trichlorobenzene–dechlorinating methanogenic microbial consortium*, Appl. Environ. Mircrobiol., 63(4): 1225–1229 (1997).

Morris, P.J., Mohn, W.W., Quensen, III, J.F., Tiedje, J.M. and Boyd, S.A., *Establishment of a Polychlorinated biphenyl–degrading enrichment culture with predominantly meta dechlorination*, Appl. Environ. Microbiol., 58(9):3088–3094 (1992).

Nies, L. and Vogel, T.M., *Effects of organic substrates on dechlorination of Aroclor 1242 in anaerobic sediments*, Appl. Environ. Microbiol., 56:2612–2617 (1990).

Nies, L. and Vogel, T.M., *Identification of the proton source for the microbial reductive dechlorination of 2,3,4,5,6–pentachlorobiphenyl*, Appl. Environ. Microbiol., 57(9): 2771–2774 (1991).

Altschul, S.F., Gish, W., Miller, W., Myers, E.W., and Lipman, D.J., *Basic Local Alignment Search Tool*, J. Mol. Biol., 215:403–410 (1990).

Cato, E.P., Geaorge, W.L., and Finegold, S.M., *Colostridium*, pp. 1141–1200, in Sneath, P.H.A., Mair, N.S., Sharpe, M.E., and Holt, J.G. (ed.), Bergey's Manual of Systematic Bacteriology, vol. 2, Williams and Wilkins, Baltimore (1986).

Ferris, M.J., Muyzer, G., and Ward, D.M., *Denaturing Gradient Gel Electrophoresis Profiles of 16S rRNA–Defined Populations Inhabiting a Hot–Spring Microbial Mat Community*, Appl. Environ. Microbiol., 62: 340–346 (1996).

Godon, J.J., Zumstein, E., Dabert, P., Habouzit, F., and Moletta, R., *Molecular Microbial Diversity of an Anaerobic Digestor as Determined by Small–Subunit rDNA Sequence Analysis*, Appl. Environ. Microbiol., 63: 2802–2813 (1997).

Grey, C.T., and Gest, H., Biological Formation of Molecular Hydrogen Science, 148: 186–192 (1965).

Grey, J.P., and Herwig, R.P., *Phylogenetic Analysis of the Bacterial Communities in Marine Sediments*, Appl. Environ. Microbiol., 62:4049–4059 (1996).

Hanson, D., *EPA Study Points to Health Risks of Dioxins and Similar Compounds*, Chem. Eng. News., 72:13–14 (1994).

Klappenbach, J.A., Dunbar, J.M., and Schmidt, T.M., *rRNA Operon Copy Number Reflects Ecological Strategies of Bacteria*, Appl. Environ. Microbiol., 66:1328–1334 (2000).

Lane, D.J., Pace, B., Olsen, G.J., Stahl, D.A., Sogin, M.L., and Pace, N.R., *Rapid Determination of 16S Ribosomal Sequences for Phylogenetic Analysis*, Proc. Natl. Acad. Sci. USA., 82:6955–6959 (1985).

Li, L., Kato, C., and Horikoshi, K., *Microbial Diversity in Sediments Collected from the Deepest Cold–seep Area*, The Japan Trench. Mar. Biotechnol., 1:391–400 (1999).

Magot, M., Ravot, G., Campaignolle, X., Ollivier, B., Patel, B.K., Fardeau, M.L., Thomas, P., Crolet, J.L., and Garcia, J.L., *Dethiosulfovibrio Peptidovorans Gen. Nov., sp. nov., A New Anaerobic, Slightly Halophilic, Thiosulfate–Reducing Baterium from Corroding Offshore Oil Wells*, Int. J. Syst. Bateriol., 47:818–824 (1997).

Magurran, A.E., Ecological Diversity and its Measurement, Princeton University Press, New Jersey (1988).

Maidak, B.L., Cole, J.R., Lilbrun, T.G., Parker Jr., C.T., Saxman, P.R., Stredwick, J.M., Garrity, G.M., Li, B., Olsen, G.J., Pramanik, S., Schmidt, T.M., and Tiedje, J.M., *The RDP (Ribosomal Database Project) Continues*, Nucleic Acids Res., 28: 173–174 (2000).

Muyzer, G., de Wall, E.C., and Uitterlinden, A.G., *Profiling of Complex Microbial Populations by Denaturing Gradient Gel Electrophoresis Analysis of Polymerase Chain Reaction Amplified Genes Coding for 16S rRNA*, Appl. Environ. Microbiol., 59:695–700 (1993).

NRC, N.R.C., *Hormonally Active Agents in the Environment*, National Academy Press (1999).

Torsvik, V., Goksoyr J., and Daae, F.L., *High Diversity in DNA of Soil Bateria*, Appl. Environ. Microbiol., 56:782–787 (1990).

Wu, Q., Sowers, K.R., and May, H.D., *Establishment of a Polychlorinated Biphenyl–Dechlorinating Microbial Consortium, Specific for Doubly Flanked Chlorines, in a Defined, Sediment–Free Medium*, Appl. Environ. Microbiol., 66:49–55 (2000).

Natarajan, M.R., Wu, W.M., Sanford, R., and Jain, M.K., *Degradation of Biphenyl by Methanogenic Microbial Consortium*, Biotechnology Letters, 21:741–745 (1999).

* cited by examiner

TABLE 1

| PCB CONGENER | PRODUCTS DETECTED AT: | | |
|---|---|---|---|
| | DAY 14 | DAY 28 | DAY 56 |
| 2-CB | NONE | NONE | NONE |
| 3-CB | NONE | NONE | NONE |
| 4-CB | NONE | NONE | NONE |
| 2,3-CB | NONE | NONE | NONE |
| 2,4-CB | NONE | NONE | NONE |
| 2,5-CB | NONE | NONE | NONE |
| 2,6-CB | NONE | NONE | NONE |
| 3,4-CB | NONE | NONE | NONE |
| 3,5-CB | NONE | NONE | NONE |
| 2,3,4-CB | 2,4-CB | 2,4-CB | 2,4-CB |
| 2,3,5-CB | NONE | NONE | 3,5-CB |
| 2,3,6-CB | NONE | NONE | 2,6-CB&2,5-CB |
| 2,4,5-CB | NONE | NONE | NONE |
| 2,4,6-CB | NONE | NONE | NONE |
| 3,4,5-CB | NONE | NONE | NONE |
| 2,3,4,5-CB | 2,4,5-CB&2,4/5-CB | 2,4,5-CB&2,4/5-CB | 2,4,5-CB&2,4/5-CB |
| 2,3,4,6-CB | 2,4,6-CB | 2,4,6-CB | 2,4,6-CB |
| 2,3,5,6-CB | 2,3,5-CB&3,5-CB | 2,3,5-CB&3,5-CB | 2,3,5-CB&3,5-CB |
| 2,3,4,5,6-CB | 2,4,6-CB | 2,4,6-CB | 2,4,6-CB&2,4-CB |
| 2,2'-CB | NONE | NONE | NONE |
| 2,2',6-CB | NONE | NONE | NONE |
| 2,2',6,6'-CB | NONE | NONE | NONE |
| 2,3,3',5,5',6-CB | | BEING TESTED | |
| 2,2',3,5,6,6'-CB | NONE | NONE | NONE |
| 2,2',3,3',5,5',6,6'-CB | NONE | NONE | 2,2'3,5,6,6'-CB |
| 2,2',3,3',4,5,5',6,6'-CB | | BEING TESTED | |

FIG. 18

TABLE 2

| PCB CONGENER | TYPE OF DECHLORINATION |
|---|---|
| 2-CB | NONE |
| 3-CB | NONE |
| 4-CB | NONE |
| 2,3-CB | NONE |
| 2,4-CB | NONE |
| 2,5-CB | NONE |
| 2,6-CB | NONE |
| 3,4-CB | NONE |
| 3,5-CB | NONE |
| 2,3,4-CB | DOUBLE FLANKED META |
| 2,3,5-CB | FLANKED ORTHO |
| 2,3,6-CB | FLANKED ORTHO & SINGLE FLANKED META (?) |
| 2,4,5-CB | NONE |
| 2,4,6-CB | NONE |
| 3,4,5-CB | NONE |
| 2,3,4,5-CB | DOUBLE FLANKED META & SINGLE FLANKED META (PARA?) |
| 2,3,4,6-CB | DOUBLE FLANKED META |
| 2,3,5,6-CB | FLANKED ORTHO |
| 2,3,4,5,6-CB | DOUBLE FLANKED META |
| 2,2'-CB | NONE |
| 2,2',6-CB | NONE |
| 2,2',6,6'-CB | NONE |
| 2,3,3',5,5',6-CB | BEING TESTED |
| 2,2',3,5,6,6'-CB | NONE |
| 2,2',3,3',5,5',6,6'-CB | SINGLE FLANKED META |
| 2,2',3,3',4,5,5',6,6'-CB | BEING TESTED |

SEQ ID NO 1 (RFLP17)

GAGTTTGATCCTGGCTCAGGATGAACGCTAGCGGCGTGCTTTATGCATGCAAGTCGAACG

GTTTTGAGTCTTCGGACTTAAAAATAGTGGCAAACGGGTGAGTAACACGTAGGTAACTT

ACCCCTAAGTTTGGGATAACTCCGGGAAACCGGGCTAATACCGGATGTGGTGAGCGGGT

AATGCCTGTTCACTAAAGCCTTCGGGCGCTTGGGGAAAGGCCTGCGTCCGATTAGCTTGT

TGGTGGGGTAATGCTCACCAAGGCTATGATCGGTAGCTGGTCTGAGAGGACGGTCAGCC

ACACTGGGACTGAGACACGGCCCAGACTCCTACGGGAGGCAGCAGCAAGGAATTTGGGC

AATGGGCGAAAGCCTGACCCAGCAACGCCGCGTGGGGGATGAAGGCCCTCGGGTTGTAAA

CCCCTTTCCCAGGAAGAATGATGACGGTACCTGGGAATAAGCCCCGGCTAACTACGT

GCCAGCAGCCGCGGTAATACGTAGGGGGCAAGCGTTATCCGGATTTACTGGGCGTAAAGA

GGACGTANGCGGCTTTCAAGTCGGATGTGAAATTCCCGGCTCAACCGGGATGAGTCAT

TCGATACTGTTGGGCTAGAGGATAGCCAGGGGAGACGGAATTCCCGGTGTAGTGGTGGAA

TACGTAGATACCGGGAGGAACACCAGAGGCGAAGGCGGTCTCCAAGGCTATTCTGACGC

TGAGGTCGAAAGCGTGGGTAGCAAACAGACTTAGATACTCTGGTAGTCCACGCTGTAAA

CGATGGACACTAGGTATAGGGAGCATCGACCCTCTTGTGCCGAAGCTAACGCTTAAGT

GTCCCGCCTGGGGACTACGGCCGCAAGGCTAAAACTCAAAGGAATTGACGGGGCCCGCA

CAAGCAGCGGAGCGTGTGGTTTAATTCGATGCAACGCGAAGAACCTTACCAAGGCTTGAC

ATGTCGGAAGTAGTGAACCGAAAGGGGAACGACCCGTTAAATCGGAGCCGTCACAGGTG

CTGCATGGCTGTCGTCAGCTCGTGCCGTGAGGTGTATGGTTAAGTCCTGCAACGAGCGCA

ACCCTCGTCAGTTGAATTCTCTAGCGAGACCGCCCTGCAAAACGGGGAGGAAGGTGG

GGATGACGTCAAGTCAGCATGGCCCTTATGCCCTGGGCTACACACGTACAATGGGTG

GTACAGCAGGTAGCAATAGGTAACCTGGAGCTAATCCCTAAAACCATCCTCAGTTCGGAT

TGTAGGCTGAAACTCGCCTGCATGAAGCTGGAGTTGCTAGTAAACGCTAGTCAGCACGGC

GCGTTGAATACGTTTCGGGCCTTGTACACACCGCCCGT

SEQ ID NO 2

ATGGCTGTGGTCAGTCGTCGTGCCGTGAGGTGTTGGTTAAGTCCTGCAACGAGC

GCAACCCTCGTTAGTTGTTTCTCTAGGCGAGACTGCCCCTGCAAAACGGGGA

GGAAGGTGGGATGACGTCAAGTCAGCATGGCCCTTATGCCTAGGCTACACA

CACGCTACAATGGGTGGTACAATTGGTTGCAATGGAGCAATCCGGAGCCAATC

CGTAAAGCCACTCTCAGTTCGGATTACAGGCTGAAACTCGCCTGTATGAAGTTG

GAGTTGCTAGTAACCGCAGGTCAGCATACTGCGGTGAATACGTTCTCGGGCCT

TGTACACACCGCCCGT

FIG.23A

SEQ ID NO 3

```
  1 cagccgccgc ggtaatacgt aggggggcaag cgttatccgg atttactggg cgtaaagagg
 61 acgtaggcgg cttttcaagt cggatgtgaa atttcccggc tcaaccggga tgagtcattc
121 gatactgttg ggctagagga tagcaggggg agacggaatt cccggtgtag tggtggaata
181 cgtagatacc gggaggaaca ccagaggcga aggcggtctc caaggctatt tctgacgctg
241 aggtccgaaa gcgtgggtag caaacagact tagatactct ggtagtccac gctgtaaacg
301 atggacacta ggtataggga gcatcgaccc tctttgtgcc gaagctaacg ctttaagtgt
361 cccgcctggg gactacggcc gcaaggctaa aactcaaagg aattgacggg ggcccgcaca
421 agcagcggag cgtgtggttt aattcgatgc aacgcgaaga accttaccaa ggcttgacat
```

```
481  gtcgggaagta gtgaaccgaa aggggaacga cccggttaaa tcgggagccg tcacaggtgc
541  tgcatggctg tcgtcagctc gtgccgtgag gtgtatggtt aagtcctgca acgagcgcaa
601  ccctcgtcgc tagttgaatt ctctagcgag accgcccctgc aaaacggggga ggaaggtggg
661  gatgacgtca agtcagcatg gcccttatgc cttgggctac acacacgcta caatggggtgg
721  tacagcaggt agcaataggg taacctggag ctaatcccta aaaccatcct cagttcggat
781  tgtaggctga aactcgccctg catgaagctg gagttgctag taaacgcgta tcagcacggc
841  gcgttgaata cgttttcggg ccttgtacac accgcccgt
```

COMPOSITIONS AND METHODS FOR MICROBIAL DECHLORINATION OF POLYCHLORINATED BIPHENYL COMPOUNDS

CROSS-REFERENCE TO RELATED APPLICATION

The priority of U.S. Provisional Patent Application No. 60/205,818 filed May 19, 2000 now abandoned in the names of Kevin R. Sowers and Harold D. May for "Compositions of Matter Useful to Dechlorinate Poly-Chlorinated Biphenyls, and Methods Related Thereto" and the priority of U.S. Provisional Patent Application No. 60/266,650 filed Feb. 6, 2001 in the names of Kevin R. Sowers and Harold D. May for "Compositions and Methods for Microbial Dechlorination of Polychlorinated Biphenyl Compounds" are hereby claimed.

GOVERNMENT RIGHTS IN INVENTION

Work relating to the invention hereof was conducted with the assistance of the U.S. Office of Naval Research, under Grant Nos. N00014-96-1-0115/0116, N00014-99-1-0078 and N00014-99-1-0101. The government may have certain rights in the invention.

BACKGROUND OF THE INVENTION

1. Field of the Invention

The present invention relates to compositions and methods for bioremediation of chlorinated biphenyls, and contemplates the use of dechlorinating microorganisms which are effective chloro substituents from biphenyl rings, including for removing ortho-chlorine substituents and doubly flanked chloro substituents.

2. Description of the Related Art

Polychlorinated biphenyls (PCBs) are haloaromatic compounds having exceptional chemical stability. Environmental and toxicological problems caused by the use of PCBs have resulted in restriction of their production under the Toxic Substances Control Act of 1976 and a complete ban of their manufacture by the United States Environmental Protection Agency in 1979. Past disposal practices have resulted in substantial PCB contamination of soils and surface water sediments. As a consequence, in the United States, at least 15% of the PCBs manufactured to date remains in the environment as a highly recalcitrant contaminant. Acute toxicological effects of PCB exposure include chloracne (a skin disease), teratotoxicity, endocrine effects, immunotoxicity, carcinogenicity, and hepatotoxicity (liver damage). The mutagenic and carcinogenic character of PCBs and their suspected role in the reproductive failure of wildlife species are issues of great concern. Further, these compounds bioaccumulate and biomagnify in the fatty tissue of animals in the food web, such as fish, which can affect the human population as a result of food consumption. In sum, the toxicological findings on PCBs and their propensity for bioaccumulation raise concern for the well-being of both humans and wildlife.

Historically, harbor regions have been heavily impacted by the accumulation of polychlorinated biphenyls due to their use in and inadvertent release from naval and industrial applications. Due to their hydrophobic character, PCBs strongly associate with organic carbon, clays and silt that settle into the anaerobic regions of marine sediments.

In aerobic environments, PCBs undergo microbial degradation with oxygen addition at the 2,3 positions by a dioxygenase and subsequent dehydration to catechol followed by ring cleavage. Although lesser chlorinated PCBs ranging from mono- to hexa-chlorinated congeners can be degraded aerobically, extensively chlorinated congeners (e.g., tetrasubstituted) such as those prominent in Aroclor 1260, a formerly commonly used PCB material, are not transformed under aerobic conditions. In this respect, most aerobic degradative activity is restricted to congeners with less than 4 to 6 chlorines, depending on the positions of the chloro substituents on the rings. This is a small region of the structural spectrum of PCBs, since there are 209 congeners (isomers and homologs) of PCBs. The substantial variety of congeners is evidence from the structure of the biphenyl molecule (see FIG. 20 herein). Commercial mixtures of PCBs formerly marketed in the United States under the Aroclor trademark typically contained more than 50 of such congeners. The extent of chlorination of the PCBs varies with the specific commercial mixture. For example, Aroclor 1242 is dominated by tri- and tetrachlorobiphenyls, the aforementioned Aroclor 1260 is dominated by penta-, hexa- and heptachlorobiphenyls, and Aroclor 1268 is dominated by hepta-, octa- and nonachlorobiphenyls. Even less-chlorinated Aroclors contain significant levels of congeners with 5 or more chlorine substituents. For this reason, even a consortium of aerobic bacteria (a consortium being a population of bacteria containing different strains with different congener (degradative) & specificity) cannot remove Aroclor PCB compositions from the environment.

Anaerobic dechlorination of PCBs is a critical step in the biodegradation of these anthropogenic compounds in anaerobic sediments. However, a general knowledge of the microorganisms responsible for these reactions has eluded prior isolation, identification and characterization efforts.

SUMMARY OF THE INVENTION

The invention relates in one aspect to isolated bioremediative microorganisms comprising a 16S ribosomal subunit nucleic acid sequence selected from the group consisting of:

(a) a nucleic acid sequence that has more than 95% identity to a nucleic acid sequence selected from the group consisting of SEQ ID NO 1 and SEQ ID NO 2, wherein the quantitative identity is readily determinable, e.g., by use of a DNAsis computer program and default parameters;

(b) a nucleic acid sequence fully complementary to a nucleic acid of (a).

The invention in additional aspects includes methods for dechlorinating chlorinated biphenyls, comprising introducing at least one microorganism of a type described herein to a system comprising chlorinated biphenyls, and providing growth conditions for the microorganism(s) such that at least one chlorine substituent per chlorinated biphenyl molecule is removed from the chlorinated biphenyl. Preferred methods include growth conditions comprising the presence of hydrogen, acetate, formate and/or fumarate, in which these agents, singly or in combinations, may be present as an additive. Methods of the invention for example include those in which the dechlorination is effected at the ortho-position of a polychlorinated biphenyl, and/or at a position at which a chloro is flanked by additional chloro substituents on one of the biphenyl rings.

The present invention contemplates in a specific aspect isolated bioremediative microorganisms comprising a 16S ribosomal subunit nucleic acid sequence selected from the group consisting of:

(a) a nucleic acid sequence that has more than 98% identity to a nucleic acid sequence of SEQ ID NO 2; and (b) a nucleic acid sequence fully complementary to a nucleic acid of (a).

The invention also contemplates methods of determining the bioremediative potential of a chlorinated biphenyl-containing site, comprising contacting a nucleic acid molecule, including a nucleic acid sequence selected from the group consisting of:
(a) a nucleic acid sequence that has more than 98% identity to a nucleic acid sequence selected from the group consisting of SEQ ID NO 1 and SEQ ID NO 2;
(b) a nucleic acid sequence fully complementary to a nucleic acid of (a),
with a nucleic acid-containing sample from the biphenyl-containing site under approximately stringent hybridization conditions, and determining positive bioremediative potential in the event that hybridization is detected.

In a further aspect, the invention relates to a method of monitoring a chlorinated biphenyl-containing site, comprising conducting serial observations using methods described herein.

The present invention in another aspect provides an enrichment culture that reductively dechlorinates 3,5-dichlorobiphenyl. The microbial catalyst has been determined by comparative sequence analysis of the microbial 16S ribosomal subunit nucleic acid sequence (16S rDNA gene). The microorganism catalyzes meta-dechlorination of correspondingly chloro-functionalized PCBs and dechlorinates a dichlorobiphenyl, a rarity in anaerobic dechlorination.

This dechlorination microbial culture can be grown away from sediment, e.g., in defined media containing <0.1% sediment.

The invention in another aspect provides an enrichment culture that reductively dechlorinates 3,3',4,4'-tetrachlorobiphenyl, as to which the microbial catalyst likewise has been determined by comparative sequence analysis of the microbial 16S ribosomal subunit nucleic acid sequence (16S rDNA gene). The microbial composition catalyzes para-dechlorination of PCBs and dechlorinates a highly toxic congener with dioxin-like characteristics to a less toxic form. This microbial dechlorination agent can be grown away from sediment, e.g., in defined media containing for example $\leq 1\%$ sediment.

The invention, inter alia, in various illustration additional aspects relates to: dechlorinating compositions comprising ortho-dechlorinating microbial strain o-17 as hereinafter described more fully; dechlorinating compositions comprising double flank-dechlorinating strain DF-1 as also described more fully hereinafter; isolates as well as consortia of the various dechlorinating species; probes based on dehalogenating gene sequences; related screening techniques based on such probes to detect PCB dechlorinating agents, e.g., in the environment; and genes encoding PCB dechlorinating enzymes.

The present invention provides compositions and methods for anaerobically degrading extensively chlorinated congeners to primarily mono- and dichlorobiphenyls, and in one illustrative aspect contemplates the treatment of PCBs with an anaerobic consortium of bacteria, followed by treatment with an aerobic consortium of bacteria, to maximize the overall degradation of PCBs.

The present invention facilitates bioremediation treatment in which dechlorination composition(s) of the invention can be seeded into clean sediments, to provide sedimentary composition(s) comprising the clean sediment material, mixed with nutrients and dechlorinating microorganisms. The sedimentary composition including the active microbial agent can be deposited over PCB-contaminated material at sites containing PCBs, such as marine or riparian sites having native sediments contaminated with PCBs, landfill sites containing PCB waste, etc. Such "capping treatment" approach has major advantages over current PCB contamination removal techniques, such as dredging of river and ocean sites, which are simply relocation measures and do not provide in situ elevation of PCBs at the locus of contamination.

The invention may also be variously embodied to carry out corresponding processes for treatment of water containing PCBs. In such processes, the dechlorinating composition of the invention can be presented in a fixed bed, bioreactor, biofilter, etc., for continuous treatment of PCB-contaminated water by flow thereof through the dedicated treatment system.

The invention, as will be appreciated more fully from the ensuing description, provides a fundamental advance in the art of treatment and destruction of PCBs, and may be applied in a wide variety of potential uses and applications for abating of PCBs, as will be appreciated by those skilled in the art.

As used herein, the following terms shall have the following meanings:

"additive" means an agent such as hydrogen, acetate, formate, fumarate, etc., that may be added to the naturally-occurring or synthetic poly-chlorinated biphenyl-containing system, in order to facilitate, enhance, or catalyze the dechlorination action being effected (the means for addition of the additive is not critical; for example, the additive may be poured, mixed, bubbled or otherwise added to the contaminated material in the process, with or without the microbial culture, and before or after microbial culturing has taken place;

"flanked" in reference to a chlorinated biphenyl means that a chlorine on the biphenyl ring is between adjacent halo (chloro) groups at each of at adjoining positions on the ring—for example, if a chlorine is present at a para position, then halo groups must be present at both meta positions on that ring in order for the chlorine to be flanked; in another example, if a chlorine is present at a meta position, then halo groups must be present at the adjoining ortho and para positions on that ring in order for the chlorine to be "flanked."

As used herein, the term "a" or "an" in reference to an entity is to be understood as referring to one or more of that entity. For example, "a microoganism" or "a nucleic acid molecule" refers to one or more of those compounds, or at least one of the compounds.

The terms "comprising", "including" and "having" can be used interchangeably.

As used herein, a compound "selected from the group consisting of" refers to one or more compounds or species on the list that follows such phrase, including mixtures (e.g., combinations) of two or more of the compounds or species.

An isolated, or biologically pure, microorganism or nucleic acid molecule is a compound that has been removed from its natural milieu. As such, the terms "isolated" and "biologically pure" do not necessarily reflect the extent to which the compound has been purified. An isolated compound of the present invention can be obtained from its natural source, or it can be produced using molecular biology techniques, or alternatively it can be produced by chemical synthesis.

Other aspects, features and embodiments of the invention will be more fully apparent from the ensuing disclosure and appended claims.

BRIEF DESCRIPTION OF THE DRAWINGS

FIG. 18 is a tabulation of PCB congeners, and products thereof at day 14, day 28 and day 56.

FIG. 19 is a tabulation of PCB congeners, showing the dechlorination modality thereof.

FIG. 21 is a depiction of SEQ ID NO. 1.

FIG. 22 is a depiction of SEQ ID NO 2.

FIG. 23 is a depiction of SEQ ID NO 3.

DETAILED DESCRIPTION AND PREFERRED EMBODIMENTS OF THE INVENTION

Figure 1:
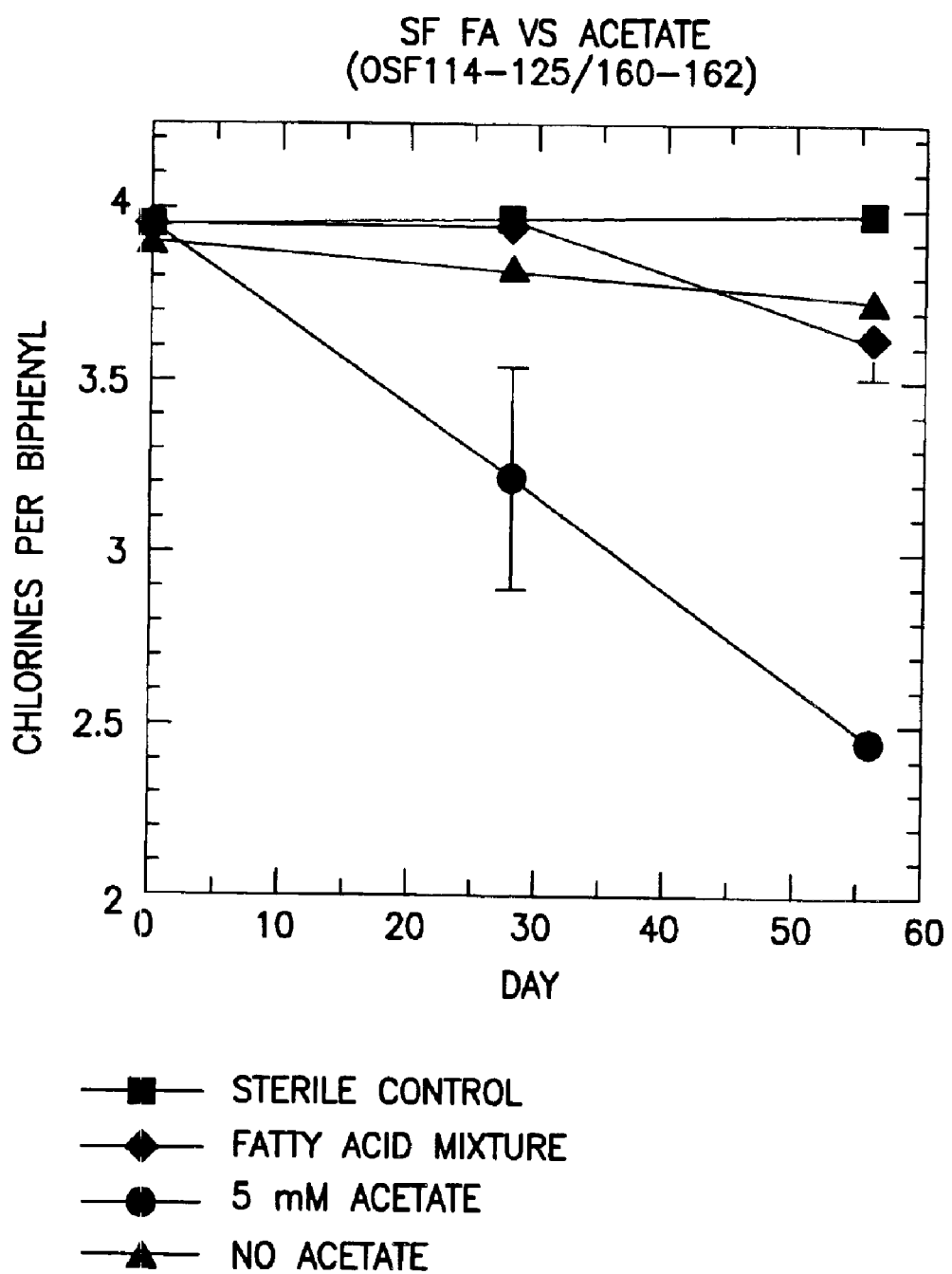
FIG. 1 is a graph of chlorines per biphenyl, as a function of time, and showing the effect of acetate addition on the dechlorination process.

Relative to the present invention and its features, aspects and embodiments as more fully described hereinafter, the disclosure of U.S. Provisional Patent Application No. 60/205,818 filed May 19, 2000 in the names of Kevin R. Sowers and Harold D. May for "Compositions of Matter Useful to Dechlorinate Poly-Chlorinated Biphenyls, and Methods Related Thereto" and the disclosure of U.S. Provisional Patent Application No. 60/266,650 filed Feb. 6, 2001 in the names of Kevin R. Sowers and Harold D. May for "Compositions and Methods for Microbial Dechlorination of Polychlorinated Biphenyl Compounds" are hereby incorporated herein by reference in their respective entireties.

The present invention includes the use of bioremediative microorganisms comprising a 16S ribosomal subunit nucleic acid sequence selected from the group consisting of:

(a) a nucleic acid sequence that has more than 95% identity, and preferably more than 98% identity, to a nucleic acid sequence selected from the group consisting of SEQ ID NO 1, SEQ ID NO 2, and SEQ ID NO 3 wherein the quantitative identity is readily determinable, e.g., by use of a DNAsis computer program and default parameters;

(b) a nucleic acid sequence fully complementary to a nucleic acid of (a).

Illustrative bioremediative microorganisms having utility in the practice of the invention include microorganisms disclosed more fully hereinafter.

The invention enables the effective dechlorination of chlorinated biphenyls, involving the provision in the chlorinated biphenyl-containing environment of growth conditions for the microorganism(s) such that chlorine is at least partially removed from the chlorinated biphenyl. The microbial dechlorination process is advantageously carried out in the presence of appropriate additives necessary or desirable for dechlorinative action on PCBs being treated. Non-limiting examples of additives that may be used in the practice of the invention include hydrogen, acetate, formate and/or fumarate, as for example may be added to the chlorinated biphenyl-containing environment being treated. For example, dechlorination s may be carried out under sufficient conditions to effect dechlorination of flanked chlorine of poly-chlorinated biphenyl present in the environment being treated by the microbial species, utilizing appropriate additives/growth conditions.

The invention in one aspect may be employed to determine the bioremediative potential of a chlorinated biphenyl-containing site, by contacting a nucleic acid sequence of the type(s) described above with a nucleic acid-containing sample from the biphenyl-containing site under hybridization conditions of suitable stringency, and determining positive bioremediative potential by detection of hybridization of the respective nucleic acid sequences.

Such hybridization methodology may also be carried out in an intermittent fashion to monitor the progress of bioremediation efforts conducted in accordance with the invention.

The compositions and methods of the invention may be employed to biodegrade halogenated organic waste, e.g., contaminated soil from landfill sites, river beds, etc., containing PCBs, as well as to treat leachates and aqueous surfactant solutions resulting from washing the aforementioned organic waste to transfer PCBs to the aqueous surfactant solutions. Surfactants potentially useful for such purpose of washing contaminated organic wastes include alkylbenzene sulfonate surfactants, e.g., Surco 233 (Onyx Chemical Co., Jersey City, N.J.), a sodium salt of an alkylbenzene sulfonate.

The invention contemplates treatment of a PCB-containing environment by inoculation or other introduction of microbially effective agents of the invention to the environment. For example, dechlorinating bacteria in accordance with the invention may be dispersed on a landfill site under appropriate conditions for effect biodegradative action on PCBs in the environment. Such dispersant may include the microbial agent in a nutrient medium, particularly if the PCB-containing environment is nutrient-deficient for such microbial species. The level of biodegradation of the PCBs can be monitored continuously or intermittently to determine the effectiveness of the microbial treatment.

The dechlorination/bioremediation processes of the present invention may if desired be advantageously combined with other bioremediation and waste-degradation methods conventionally employed in the art, to achieve an enhanced decontamination or purification result. The methods of the following U.S. patents, herein incorporated by reference in their entireties, are illustrative: U.S. Pat. No. 5,968,360 (composition and method for degradation of polychlorinated biphenyls in soil), U.S. Pat. No. 5,635,393 (method for dechlorinating polychlorinated biphenyls and granules for use therein), U.S. Pat. No. 5,618,727 (bioremediation process design utilizing in situ soil washing), U.S. Pat. No. 5,540,838 (stimulation of microbial para-dechlorination of polychlorinated biphenyls), U.S. Pat. No. 4,876,201 (method for biodegrading PCBs), U.S. Pat. No. 5,932,472 (method for degradation of polychlorinated biphenyls in soil), U.S. Pat. No. 5,858,692 (polychlorinated biphenyls (PCB) immunoassay method, its components and a kit for use in performing the same), U.S. Pat. No. 5,834,222 (polychlorinated biphenyls (PCB) immunoassay method, its components and a kit for use in performing the same), U.S. Pat. No. 5,750,065 (adsorption of PCBs using biosorbents), U.S. Pat. No. 5,242,601 (sludge treatment with CaO or $CaC_2$ and recovery of CaO therefrom), and U.S. Pat. No. 4,950,309 (process for the conversion of toxic organic substances to useful products).

The compositions and methods of the invention may be employed for anaerobically degrading extensively chlorinated congeners to primarily mono- and dichlorobiphenyls, e.g., involving the treatment of PCBs with an anaerobic consortium of bacteria in accordance with the invention, followed by treatment with an aerobic consortium of bacteria, to maximize the overall degradation of PCBs.

The invention therefore contemplates the treatment highly chlorinated PCBs by an anaerobic consortium of microbial species (species that are anaerobically effective for dechlorination of the highly chlorinated congeners), followed by treatment of the correspondingly anaerobically degraded PCBs with an aerobic consortium of microbial species (that are aerobically effective for dechlorination of the partially degraded PCBs).

Such treatment may for example be conducted at a PCB-containing site, e.g., including water, soil and/or sediment, or otherwise with respect to a separated or recovered PCB-containing material or isolated PCBs, in which one or more PCB-degrading anaerobic microorganisms is brought into degradative relationship with the PCB(s) to effect at least partial dechlorination of the PCB(s) under conditions effective for such microbial action. The dechlorinating action may include removal of chlorine substituents from the ortho position of a ring of the PCB, and/or removal of chlorine substituents that are double-flanked by other chloro substituents on the biphenyl ring structure. The microbial consortia employed for such purpose may further contain or be followed in the treatment flow sequence by organisms specifically adapted for dechlorination of para- and meta-chloro substituents, to provide a comprehensive dechlorination treatment of the PCB(s).

Figure 16:
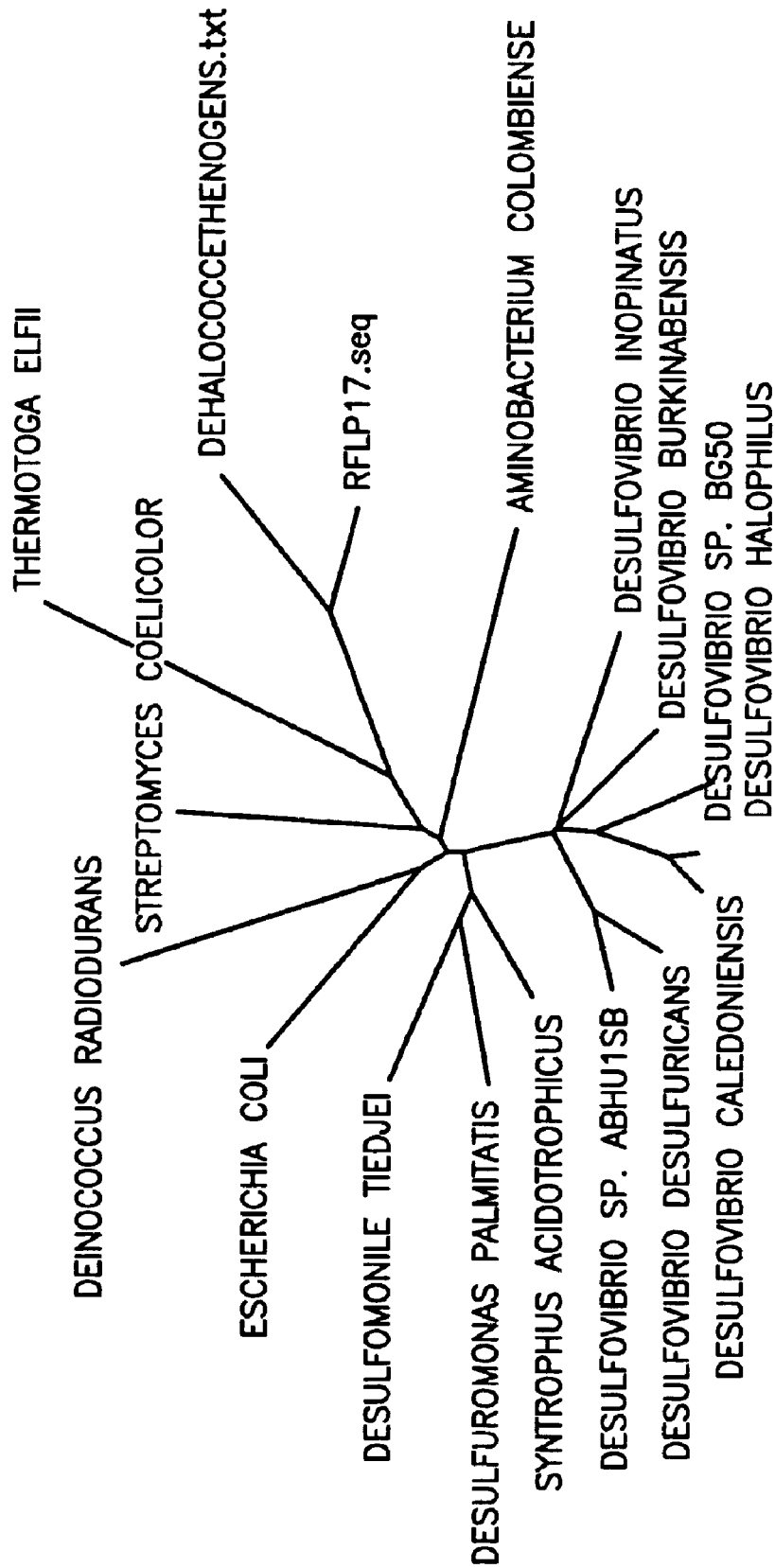
FIGS. 16 and 17 are phylogenetic charts of microbial species including species advantageously employed in the practice of the present invention.
Figure 17:
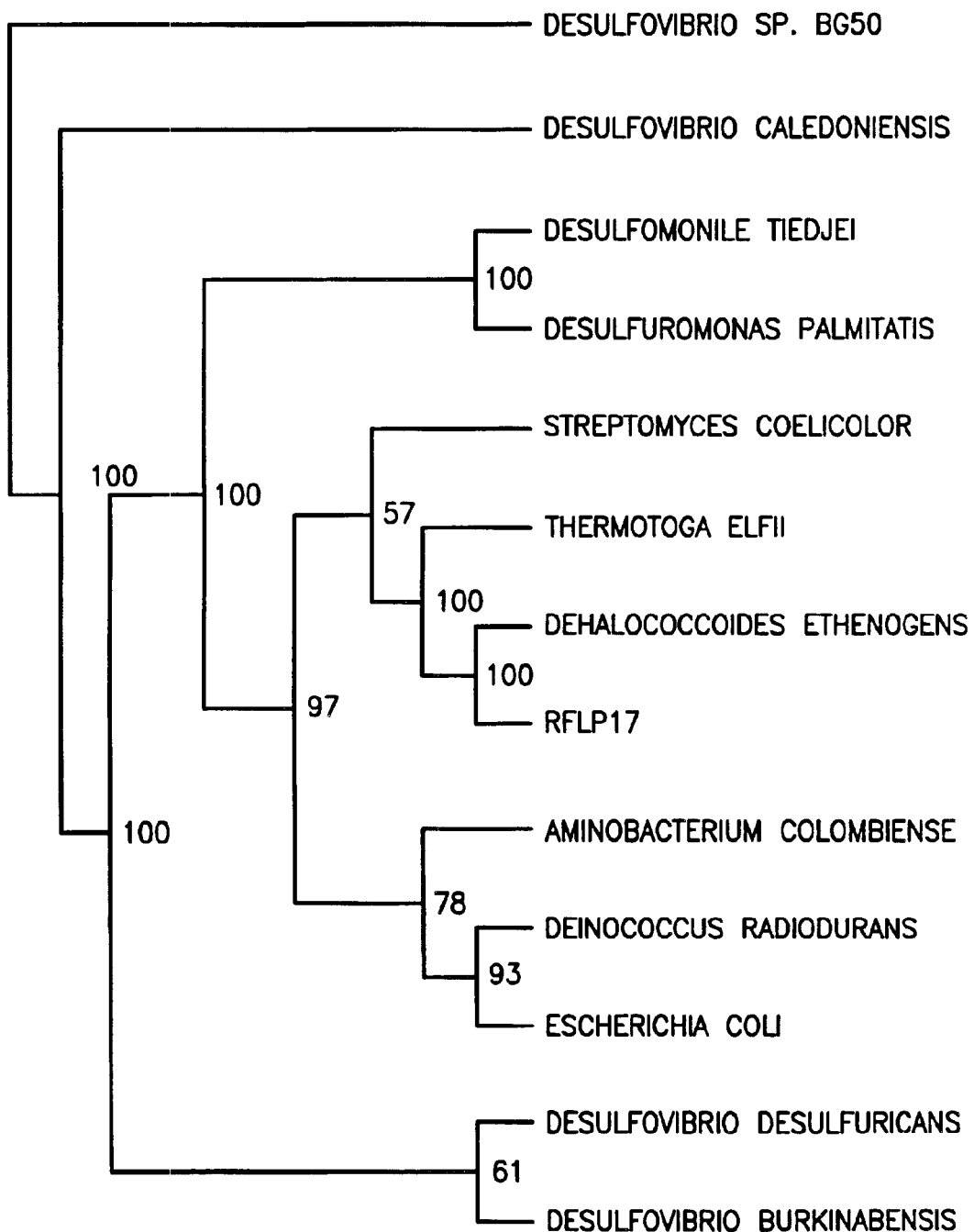
Figure 20:
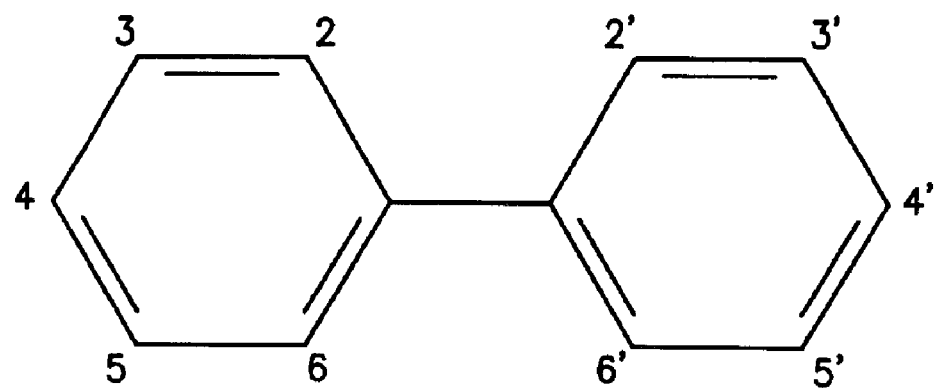
FIG. 20 is a schematic representation of a biphenyl structure with the ring substituent positions shown thereon.

Microbial species potentially useful in the consortia employed for PCB dechlorination include those in the phylogenetic depictions of FIGS. 16 and 17.

The invention in specific embodiments utilizes dechlorinating compositions comprising ortho-dechlorinating microbial strain o-17 (a sequence having 100% identity to SEQ ID NO 3) and/or double flank-dechlorinating strain DF-1 (a sequence having 89% identity to SEQ ID NO 3), where these strains may be present singly, or alternatively in a consortium of microbial strains of diverse character having corresponding activity for dechlorination of variant PCB congener structures.

The treatment methods and compositions of the invention do not require a methanogenic consortium, and do not require formation of granules. Further, particular dechlorinating microbial species may be employed, e.g., ortho-dechlorinating microbial strain o-17 and double flank-dechlorinating strain DF-1, that may be grown with only single fatty acids: o-17 requires only acetate, and DF-1 requires only formate.

Probes and primers are also contemplated by the present invention. Primers of the present invention can be designed by alignment of 16S regions from at least two PCB-dechlorinating species, and identification of primers that amplify amplicons specific for those microorganisms and capable of priming polymerase chain reaction (PCR). Primers are preferably G-C rich in character, with more than 50% of the bases therein desirably being G or C. The length of a primer is suitably chosen to minimize the occurrence of amplification of non-target nucleic acid, as well as to minimize the occurrence of self-hybridization. Primers are typically 17 to 30 bases in length, but primers of any suitable length and G-C content may be usefully employed. Commercially available computer programs, e.g., MacVector, may be employed in the primer design effort and for optimizing PCR conditions. The sequences described herein can be shortened from the 5' end, provided that the corresponding sequence does not lose specificity when used as a primer.

The scope of the present invention, with respect to the nucleic acids discussed above, allelic variants, degenerate sequences, and homologs, as well as use of variants produced by laboratory manipulation, e.g., variants produced during PCR amplification or site-directed mutagenesis. In respect of redundancy in codons coding for specific amino acids, the invention comprehends the use of nucleic acid sequences that contain alternative codons for expression of the same amino acid. The invention further comprehends the use of mutations in nucleic acid sequence or translated protein that do not substantially alter or preclude the desired physical properties of the expressed protein. Mutations of such type may for example include substitution of valine for leucine, arginine for lysine, and/or asparagine for glutamine. Additionally, nucleic acid sequences are contemplated by the invention that are homologous to the exemplified nucleic acid molecules (or allelic variants or degenerates thereof), that have at least 85%, more preferably at least 90%, and most preferably at least 95% sequence identity with a nucleic acid sequence specified in the sequence listing hereof.

The invention further comprehends the provision and use of isolated nucleic acids having at least 100 contiguous nucleotides of the sequence of SEQ ID NO 1 or SEQ ID NO 2. "At least" in such context means that this is a lower limit, and that the number of contiguous nucleotides of the sequence can be any whole number increment up to the total number of bases in SEQ ID NO 1 or SEQ ID NO 2, e.g., isolated sequences in which the number of contiguous nucleotides is 25, 50, 75, 100, 125, 150, 200, 225, etc. are within the scope of the invention.

Commercially available computer programs may be employed to determine the degree of similarity between two nucleic acid sequences. Such computer programs utilize various known methods to determine the percent identity and the number and length of gaps between hybrid nucleic acid molecules, and the percent identity among amino acid sequences or nucleic acid sequences. Computer programs for comparison and analysis of nucleotide and amino acid sequences include, without limitation, GCG™ software (Genetics Computer Group, Madison, Wis.), DNAsis™ software (Hitachi Software, San Bruno, Calif.), MacVector™ software (Eastman Kodak Company, New Haven, Conn.), etc. A preferred method to determine percent identity among amino acid sequences and also among nucleic acid sequences includes using the Compare function by maximizing matching within the program DNAsis™ Version 2.1 using default parameters.

Knowing the nucleic acid sequences specified herein, one skilled in the art can (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain similar nucleic acid molecules from other species. Such nucleic acid molecules can be obtained in a variety of ways, including screening appropriate expression libraries with antibodies; applying traditional cloning techniques using oligonucleotide probes to screen appropriate libraries of DNA; and employing PCR amplification of appropriate libraries of DNA using oligonucleotide primers of the present invention. Preferred libraries to screen or from which to amplify nucleic acid molecules include canine cDNA libraries as well as genomic DNA libraries. Similarly, preferred DNA sources to screen or from which to amplify nucleic acid molecules include adult cDNA and genomic DNA. The methods for conducting these types of molecular manipulations are well-known in the art, and are described in detail in Sambrook et al., Molecular Cloning. A Laboratory Manual (Cold Spring Harbor Laboratory Press, 1989) and Ausubel, et al., Current Protocols in Molecular Biology (Greene Publishing Associates, Inc., 1993).

The present invention also includes nucleic acids that are oligonucleotides capable of hybridizing, under suitable hybridization stringency conditions, with complementary regions of other, preferably longer, nucleic acid molecules of the present invention. Oligonucleotides of the present invention can be RNA, DNA or derivatives of either. The minimum size of such oligonucleotides is the size required for formation of a stable hybrid between an oligonucleotide and a complementary sequence on a nucleic acid molecule of the present invention. Minimal size characteristics are disclosed herein. The present invention includes oligonucleotides that can be used, for example, as probes, to identify nucleic acid molecules, as primers to produce nucleic acid molecules, as primers to produce nucleic acid molecules or as therapeutic agents.

Stringent hybridization conditions are determined based on defined physical properties of the gene to which the nucleic acid molecule is being hybridized, and can be defined mathematically. Stringent hybridization conditions are readily determined within the skill of the art to allow identification of significant similarities between heterologous nucleic acid molecules. See, for example, Sambrook, et al., 1989, Molecular Cloning: A Laboratory Manual, Cold Spring Harbor Labs Press, and Meinkoth, et al., 1984, Anal. Biochem. 138, 267–284.

The features and advantages of the invention are more fully apparent from the following illustrative examples, which are not intended in any way to be limitingly construed, as regards the invention hereinafter claimed. In the ensuing examples, the reactions and manipulations involving DNA techniques, unless otherwise stated, were performed as described in Sambrook, et al., 1989, Molecular Cloning: A Laboratory Manual, Cold Spring Harbor Labs Press, the disclosure of which hereby is incorporated herein by reference.

EXAMPLE 1

Methods and Materials for Development of 2,3,5,6-CB Ortho-Dechlorinating Consortia Sediment Sample. Core samples (41×5 cm) of sediment were taken 8 meters below the surface water in the Inner Harbor of Baltimore, Md. Baltimore Harbor (BH) sediments were black in color, gelatinous in texture and had a strong petroleum odor. The salinity of the water column immediately above the sediments was 10 ppt at the time of the sampling. The lower 30 cm of sediment was immediately transferred to a glass container that had been purged with nitrogen. Sodium sulfide nonahydrate was added to a final concentration of 0.018% (wt/vol), and the vessel was sealed under the nitrogen with a butyl rubber stopper. The sediment sample was stored at room temperature in the dark prior to use.

Culture conditions. All media in these experiments included modified basal medium composed of the following components in grams per liter (final concentration) of demineralized water: $Na_2CO_3$, 3.0; $Na_2HPO_4$, 0.6; $NH_4Cl$, 0.5; cysteine-$HCl.H_2O$, 0.25; $Na_2S$ $9H_2O$, 0.25; resazurin, 0.001. In addition, 1% (v/v) each of vitamin and trace element solutions was added. Estuarine medium without sulfate contained the following components in grams per liter (final concentration) of basal medium: NaCl, 8.4; $MgCl_2$ $6H_2O$, 3.95; KCl, 0.27; $CaCl_2.2H_2O$, 0.05. Estuarine salts medium with sulfate contained the following components in grams per liter (final concentration) of basal medium: NaCl, 8.4; $MgCl_2$ 6H2O, 4.44; KCl, 0.27; $CaCl_2$.2H2O, 0.05. Marine salts medium with sulfate contained the following components in grams per liter (final concentration) of basal medium: NaCl, 23.38; $MgCl_2$ $6H_2O$, 12.32; KCl, 0.76; $CaCl_2.2H_2O$, 0.014. Sterile media were prepared anaerobically in an atmosphere that contained $N_2$—$CO_2$ (4:1) by a modification of the Hungate technique. All gases were passed through a column of reduced copper turnings at 350° C. to remove traces of $O_2$. Media (8 ml) were dispersed into culture tubes (16×160 mm) and sealed with Teflon®-lined butyl stoppers (The West Company, Lionville, Pa.) secured by aluminum crimp collars (Bellco Glass, Inc., Vineland, N.J.).

BH sediments (10% vol/vol) were inoculated into media and incubated with individual PCB congeners at the following final concentrations in micromols per liter: monochlorobiphenyls, 266.0; dichlorobiphenyls, 225.2; trichlorobiphenyls, 195.3; tetrachlorobiphenyls, 172.5; pentachlorobiphenyls, 154.4. Due to their low solubility in water, the congeners were solubilized in acetone before addition to the sediments. The final concentration in acetone was 0.1% (vol./vol). Sodium acetate, propionate, and butyrate were added to a final concentration of 2.5 mM each. Cultures were incubated at 30° C. in the dark. Sterile controls were autoclaved at 121° C. for 3 hrs.

Development of Sediment-Free Cultures. Primary sediment enrichment cultures were generated in culture tubes by adding 2 ml of BH sediment to 8 ml of sterile E-Cl medium (approximately 5%, wt/vol (dry weight), sediment concentration), plus a mixture of sodium acetate, propionate, and butyrate to final concentrations of 2.5 mM each. Congener 2,3,5,6-tetrachlorobiphenyl (2,3,5,6-CB) was solubilized in acetone and added to each culture to a final concentration of 173 mM (50 ppm), and this resulted in a 0.1% (vol/vol) concentration of acetone. Cultures were incubated under strict anaerobic conditions at 30° C. in the dark. Killed cell controls were sterilized in an autoclave at 121° C. for a total of 3 hours (two 1.5 hours treatments). Sequential transfers of sediment-containing cultures were made as follows. The entire sediment-containing culture was made into a suspension by shaking, and then the particulate matter was allowed to settle for approximately 1 minute. Supernatent material then was transferred in order to minimize the amount of sediment passed to the next vessel. Sequential transfers (10% (vol/vol)) from primary enrichment cultures were made into E-Cl medium with dried BH sediment (0.1%, wt/vol (dry weight), unless otherwise stated) that was then sterilized in an autoclave at 121° C. for a total of 3 hours (two 1.5 hours treatments). Subsequent transfers were made under identical conditions every 2 to 5 months. Sequential transfers (10% (vol/vol)) for the establishment of sediment-free cultures were made every 2 to 5 months into identical media without sediment. Following the first two transfers, the amount of sediment passed was negligible.

EXAMPLE 2

Method and Materials

Culture Conditions. All sterile media in these experiments included an estuarine salts medium without sulfate (E-Cl) and were prepared anaerobically in an atmosphere that contained $N_2$:$CO_2$ as previously described by Cutter et al. An anaerobic enrichment culture capable of ortho dechlorination of 2,3,5,6-tetrachlorobiphenyl (2,3,5,6-CB) in the absence of sediment was used in this study. The culture had been transferred (10% (vol/vol)) 8 times in E-Cl medium with a mixture of fatty acids (final concentration of 2.5 mM each of sodium acetate, sodium propionate, and butyrate and 173 $\mu$M (50 ppm) of 2,3,5,6-CB (solubilized in acetone). This enrichment culture is referred to herein as the ortho culture.

Where indicated, transfers (10% (vol/vol)) were made from fatty acid-fed ortho culture into fresh E-Cl medium amended with 5 mM sodium acetate (Sigma Chemicals, St. Louis, Mo.) and 173 $\mu$M (50 ppm) of 2,3,5,6-CB (AccuStandard, New Haven, Conn.). Sequential transfers (10% (vol/vol)) were then made from 5 mM acetate-fed ortho cultures into fresh E-Cl medium amended with 0 to 40 mM sodium acetate or 13.6 mM acetone and 173 $\mu$M (50 ppm) of 2,3,5,6-CB. Where indicated, acetate-fed ortho cultures were amended with bromoethanesulfonic acid (BES) (Sigma Chemicals, St. Louis, Mo.). The BES was dissolved in sterile deionized water, filter sterilized and added to a final concentration of 0.1 to 3 mM. Sequential transfers (10% (vol/vol)) were also made from 5 mM acetate-fed ortho cultures into fresh E-Cl medium under an atmosphere of $H_2$:$CO_2$ to a final concentration of 100 kPa or 250 kPa without additional acetate. All cultures were incubated under strict anaerobic conditions in the dark at 30° C. Killed cell controls were sterilized in an autoclave at 121° C. for 30 minutes. Sequential transfers were made every 1-3 months into fresh E-Cl medium with indicated amendments.

Spectrophotometric Analysis

Growth in the ortho cultures was monitored by following changes in optical density at 600 nm with a Spectronic 20D spectrophotometer (Milton Roy, Rochester, N.Y.).

Methane Determination

Analysis of methane was made with a Hewlett-Packard 5890A gas chromatograph (GC) equipped with a flame ionizer detector (FID) and an Rtx-624 capillary column. Samples of the culture headspace were drawn into a glass syringe with a gas-tight luer-lock. Samples were then injected manually onto the FID for analysis. Methane peaks were identified by retention time. Final calculations were based on total headspace volume. Standard curves were generated using samples of natural gas under the same conditions.

Culture Sampling and PCB Analysis

Aliquots were withdrawn anaerobically from shaken cultures at each time point using a 5-ml glass pipette. Ethyl acetate extraction of the PCBs from the samples and subsequent cleanup over Florisil-copper columns were done according to Cutter et al. PCB analysis was conducted with a Hewlett-Packard 5890A gas chromatograph (GC) equipped with an electron capture detector (ECD) and an RTX-1 capillary column. PCB analysis was also conducted with a Hewlett-Packard 5890A gas chromatograph (GC) equipped with an electron capture detector ($\mu$ECD) and an RTX-1 capillary column. PCB congeners were identified by retention time and quantified with a 16-point calibration curve for each congener according to the methods of Berkaw et al. Standards for 2,3,5,6-CB and the possible dechlorination products were purchased from AccuStandard (New Haven, Conn.).

Extraction of Genomic DNA

Samples (1–1.5 ml) from the ortho culture were drawn/removed under anaerobic conditions. Genomic DNA was then extracted using the Bio-Rad InstaGene Matrix (Hercules, Calif.) according to the manufacturer's instructions. Briefly, the sample was centrifuged at 12,000 rpm for 3 minutes, the supernatant was removed, and 200 $\mu$l matrix was added to the pellet. The sample was incubated at 56° C. for 30 minutes, vortexed for 10 seconds, incubated at 100° C. for 8 minutes, vortexed for 10 seconds, and then centrifuged. The resulting supernatant was used in the amplification reaction.

Amplification of 16S rDNA for DGGE Analysis

The polymerase chain reaction (PCR) was used to amplify 16S rDNA from the purified microbial community DNA. Primers 1055–1070 forward (5'-ATGGCTGTCGTCAGCT-3') (SEQ ID NO. 4) and 1406–1392 reverse (5'-ACGGGCGGTGTGTAC-3') (SEQ ID NO. 5) were utilized for the amplification of bacterial 16S rDNAs. These primers will amplify a 322-bp fragment of the 16S rRNA gene, which contains the highly variable V9 region from microorganisms within the domain Bacteria. A 40-base GC clamp was added to the 5' end of the 1406R primer to ensure that the DNA fragments do not completely denature and separate in the DOGE gel. The resulting fragment is a total of 391-bp in length.

PCR was performed using the GeneAmp PCR kit with Ampli-Taq DNA polymerase in a PE System 2400 thermocycler (Perkin Elmer, Norwalk, Conn.) according to the manufacturer's instructions with the following modifications per 50 $\mu$l reaction: 2.5 mM $MgCl_2$ solution, 0.5 Units Ampli-Taq DNA polymerase, 0.2 $\mu$M of each primer, 1.25 $\mu$l deionized formamide (Sigma Chemicals, St. Louis, Mo.) and 20 $\mu$g non-acetylated bovine serum albumin (New England BioLabs, Inc., Beverly, Mass.). The PCR cycle parameters were as follows: an initial denaturation step of 5 minutes at 94° C., 9 amplification cycles of denaturation (30 seconds at 94° C.), annealing (30 seconds at 62° C. minus 1° C. each cycle until touchdown at 43° C.) and elongation (30 at 72° C.), followed by a final elongation step at 72° C. for 5 minutes. The PCR reactions were then checked for correct size and yield on a 1% TAE high melt agarose gel (Bio-Rad, Hercules, Calif.). The amplified rDNA then was examined by DGGE analysis.

Denaturing Gradient Gel Electrophoresis (DGGE) Analysis

Electrophoresis of the amplified 16S rDNA was performed as described by Muyzer et al. using the Bio-Rad Dcode™ Universal Mutation Detection System (Bio-Rad, Hercules, Calif.). A parallel 7% (wt/vol) polyacrylamide (40% acrylamide/bis-acrylamide (37:5:1)) (Sigma Chemicals, St. Louis, Mo.) gel with a 40%-70% linear denaturing gradient formed with urea and deionized formamide was prepared using a Bio-Rad Model 385 gradient former (Bio-Rad, Hercules, Calif.). Denaturing solutions of urea (Sigma Chemicals, St. Louis, Mo.) and deionized formamide were prepared according to the manufacturer's instructions where a 100% denaturing solution is defined as 40% (vol/vol) formamide and 7M urea (Bio-Rad, Hercules, Calif.). The PCR products (X $\mu$l) were electrophoresced in 1×TAE buffer (0.04 M Tris base, 0.02 M glacial acetic acid, 1 mM EDTA) at 60° C. for 20 hours at 45 volts. The gel was stained with 20 $\mu$l 1000X SYBR Green I nucleic acid gel stain (Molecular Bio-Probes, Eugene, Oreg.) in 200 ml. 1× buffer for 15 minutes. The gel was rinsed with distilled water to remove excess SYBER stain. A Fluorimager 575 (Molecular Dynamics, Sunnyvale, Calif.) apparatus was used to visualize the gel with the following parameters: 100 micron pixel size, normal scan speed, 16 bit resolution, 1 channel, 600 PMT voltage and no filter. The contrast was adjusted using Adobe Photoshop 5.5 (Adobe Systems, Inc.)

Standards for DGGE Analysis

To allow gel-to-gel comparison, standards were generated from environmental clones, obtained from previous ARDRA analysis of the cultures. A standard was also generated from a pure culture of *Burkholderia cepacia* (ATCC, Manassas, Va.).

Sequence Analysis

Following SYBR green I staining and visualization with the Fluorimager device, the polyacrylamide gel was additionally stained with ethidium bromide (0.5 $\mu$g/ml final concentration) and visualized with an ultraviolet light source. Bands at each unique position were excised with a sterile scalpel blade and transferred to a 0.5 $\mu$l centrifuge tube. Sterile water (50 $\mu$l) was added to each tube and the tubes were placed at 4° C. overnight to elute. The elutant was transferred to a new sterile 0.5 $\mu$l centrifuge tube. PCR was used to reamplify 2 and 4 $\mu$l of the eluted 16S rDNA fragment using the primers and conditions described above. The remaining elutant was stored at −20° C. DGGE was used to analyze the reamplified 16S rDNA as described above to ensure pure isolation of the 16S rDNA fragment and to confirm the relative position of the excised band. A minimum of 2 bands representative of each unique position in the linear gradient were excised and sequenced to ensure that the band represented the same species in all the lanes.

The remaining PCR product from the amplification of the eluted 16S rDNA from excised bands was purified with the QIAquick PCR purification kit (Qiagen, Inc., Chatsworth, Calif.). The bands were then sequenced according to the methods of Ferriws et al. using an ABI 373 Automated Sequencer (Applied Biosystems, Foster City, Calif.).

Results

Figure 2:
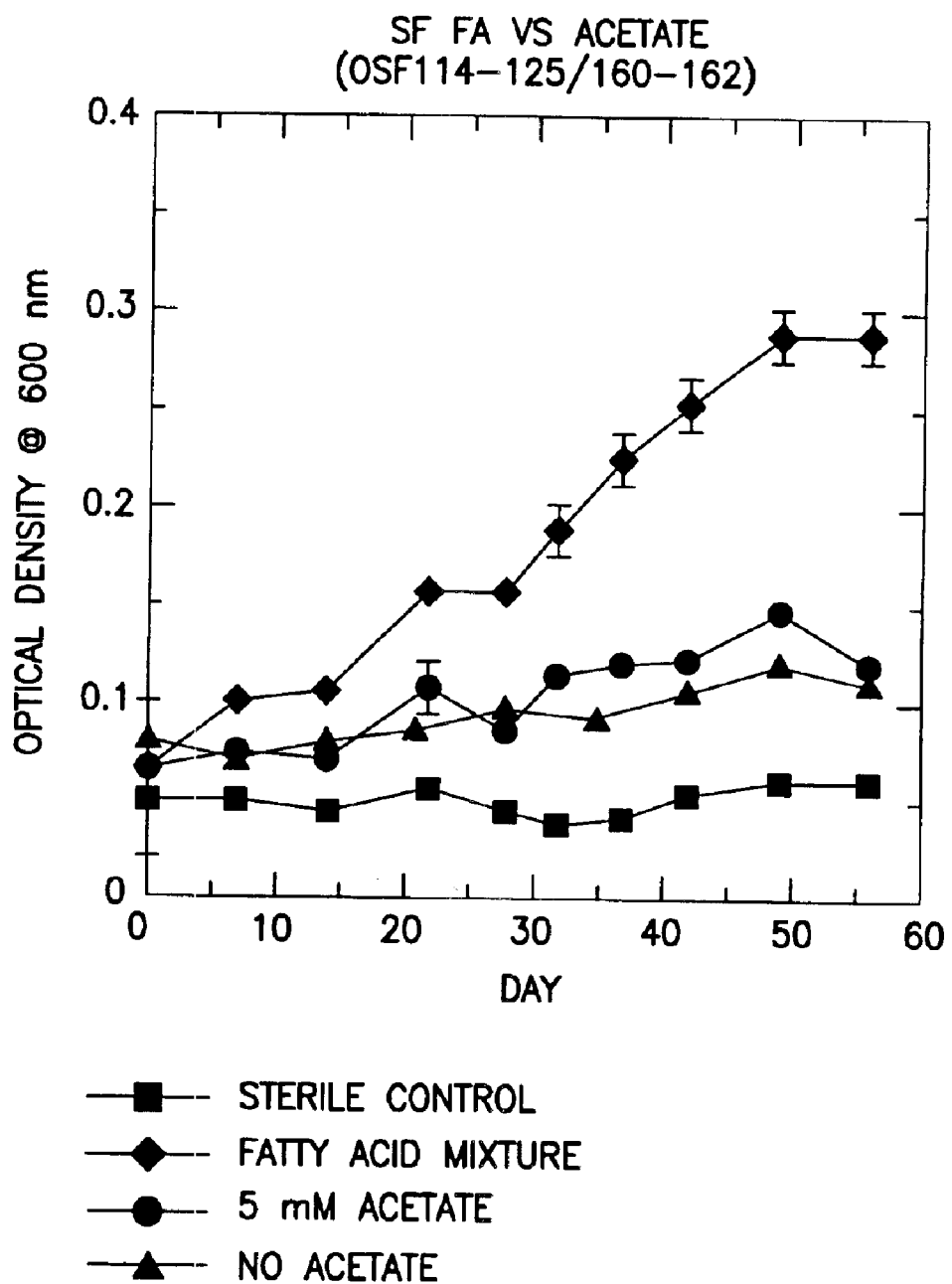
FIG. 2 is a graph of optical density of a dechlorination medium as a function of time, and showing the effect of acetate addition on the dechlorination process.
Figure 3:
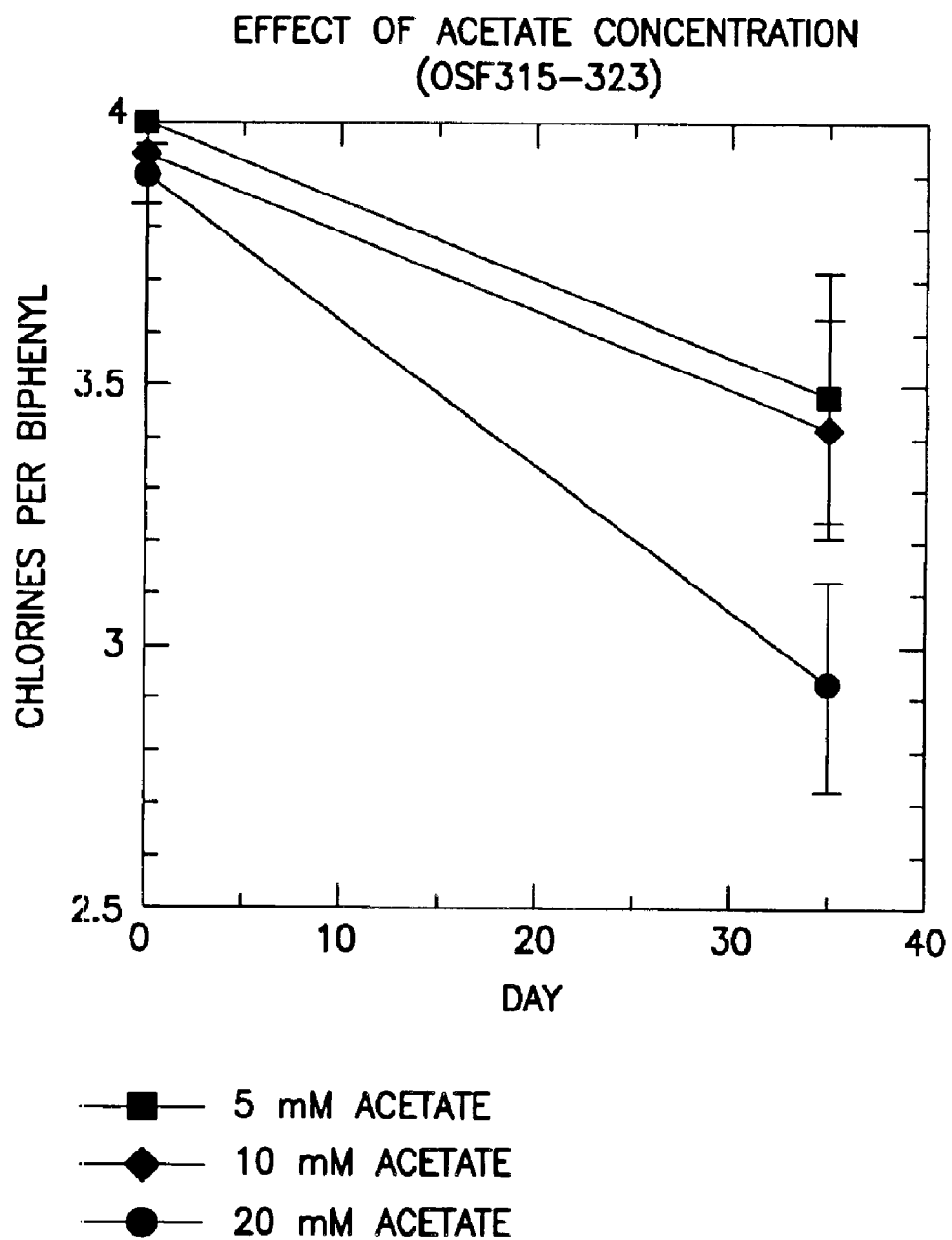
FIG. 3 is a graph of chlorines per biphenyl, as a function of time, and showing the effect of varying levels of acetate addition on the dechlorination process.
Figure 4:
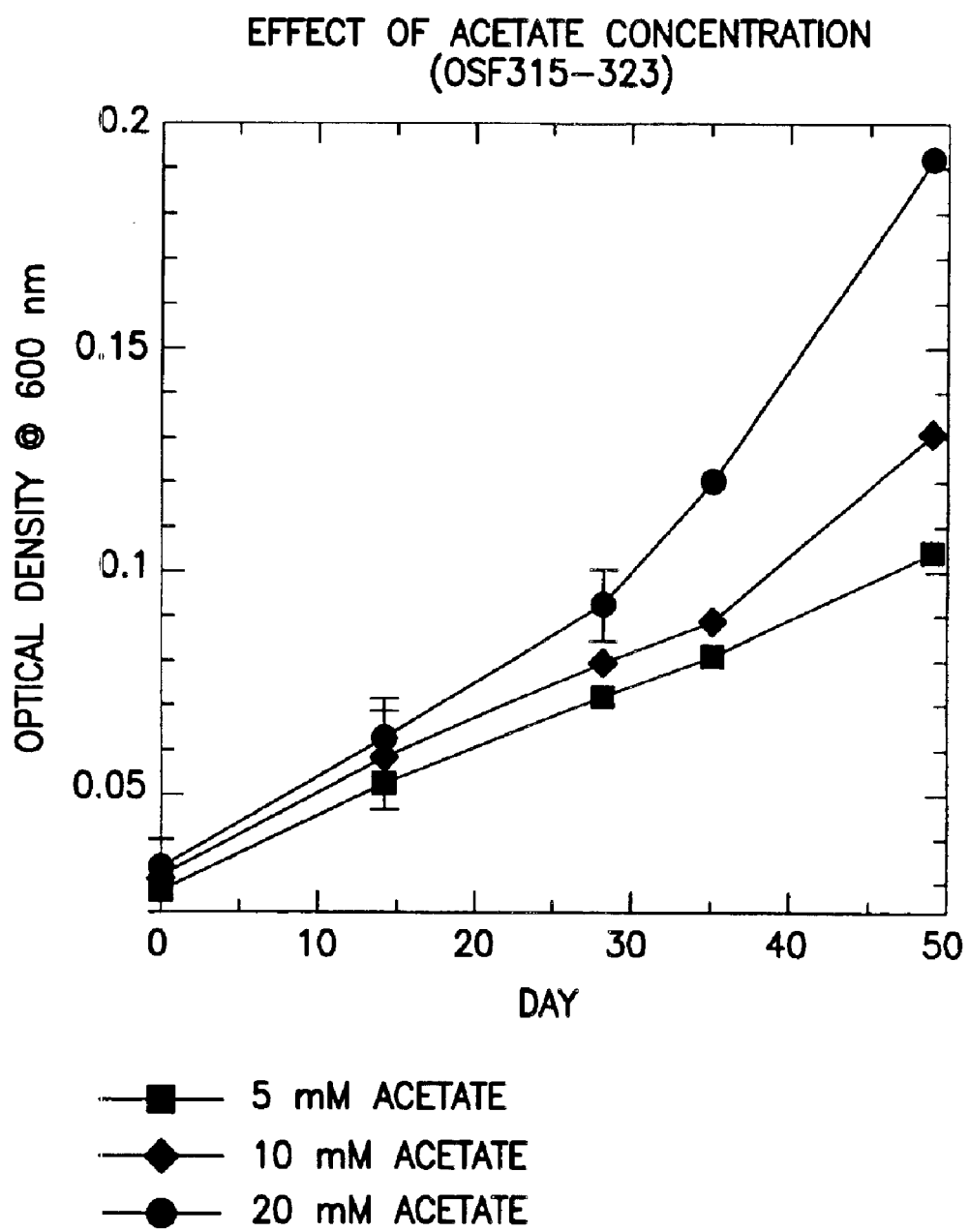
FIG. 4 is a graph of optical density of a dechlorination medium as a function of time, and showing the effect of varying levels of acetate addition on the dechlorination process.

Effect of Acetate on Dechlorination. The ortho culture was transferred from E-Cl media containing a mixture of fatty acids into fresh E-Cl media amended with 5 mM acetate. This revealed that the addition of acetate alone would support the ortho dechlorination of the 2,3,5,6-CB in the sediment-free cultures (FIG. 1). The simplification of the carbon source also enhanced PCB dechlorination in the ortho culture (FIG. 1). While more overall cell growth (based on changes in optical density) is apparent in the cultures incubated with a mixture of fatty acids, greater dechlorination is observed in the acetate cultures with no apparent lag (FIGS. 1 and 2). Higher dechlorination at lower ODs suggested a selected enrichment for organisms involved in the dechlorination of 2,3,5,6-CB. Incubation of ortho culture in the absence of acetate resulted in a complete loss of detectable dechlorination, of 2,3,5,6-CB indicated a necessity for acetate (FIG. 3).

Figure 5:
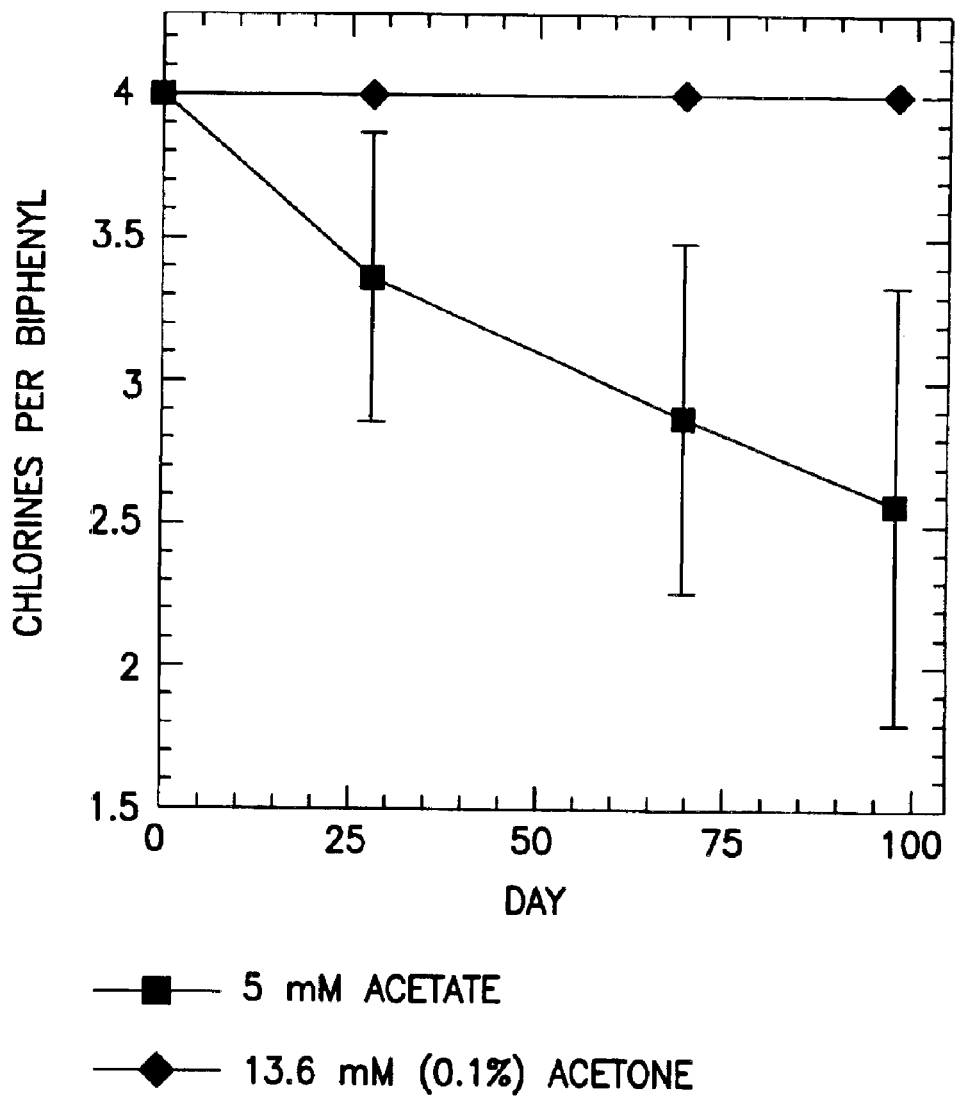
FIG. 5 is a graph of chlorines per biphenyl, as a function of time, and showing the effect of acetone addition versus acetate addition on the dechlorination process.
Figure 6:
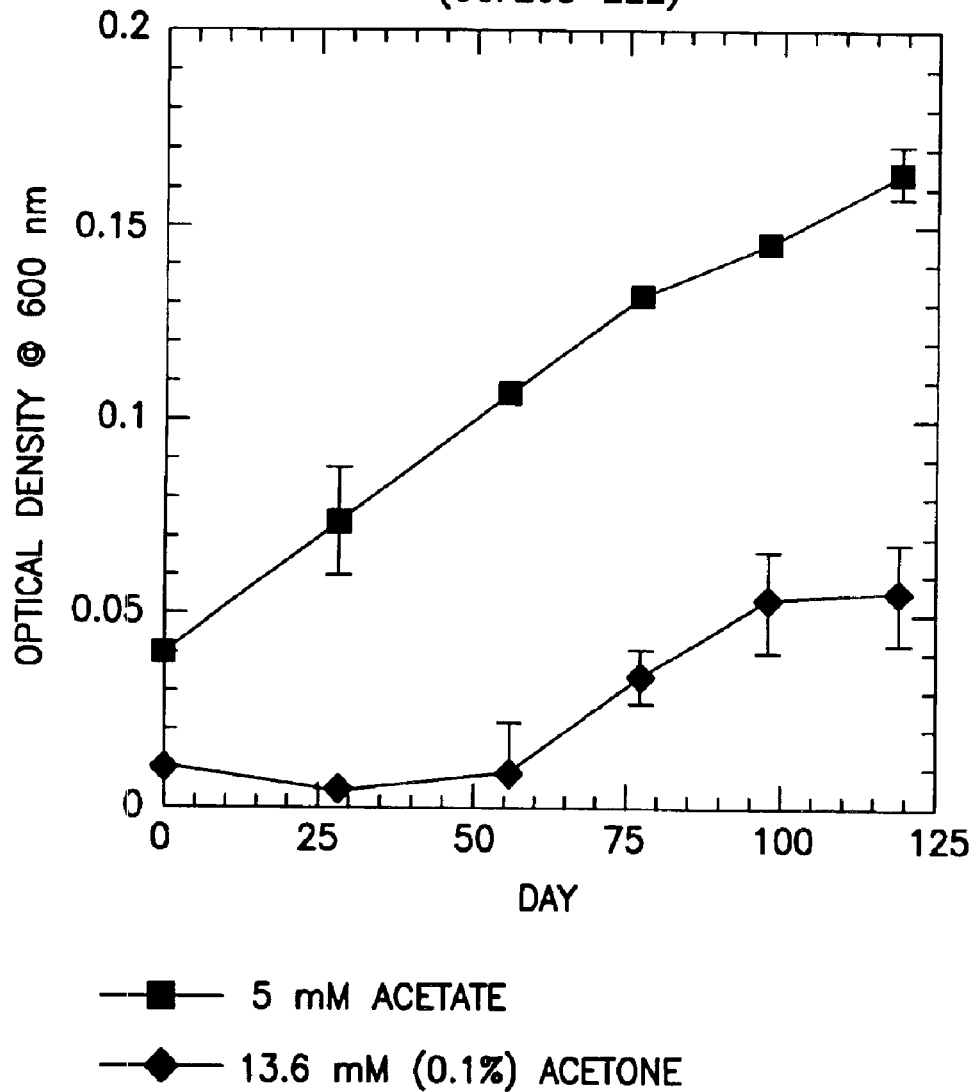
FIG. 6 is a graph of optical density of a dechlorination medium as a function of time, and showing the effect of acetone addition versus acetate addition on the dechlorination process.

To determine if the acetate-amended cultures were limited by the concentration of acetate provided, dechlorination of 2,3,5,6-CB was tested with 5, 10, 20, 30 and 40 mM acetate. Enrichment cultures supplied with 10 mM and 20 mM acetate exhibited exhibited higher ODs over time (FIG. 6). Cultures amended with 20 mM acetate also showed an increased rate of dechlorination after one month with two-times the dechlorinating activity occurring versus the cultures amended with 5 mM acetate (FIG. 5). Cultures with 10 mM acetate did not show the increased rates of dechlorination over the 5 mM acetate control. Based on the indications of stimulation of growth and dechlorination with higher acetate concentrations, transfer into higher amounts of acetate was investigated. Cultures supplied with 30–40 mM acetate did not exhibit increased rates of dechlorination above those seen with the 20 mM acetate cultures (data not shown). These data indicate enrichment for dechlorinating activity and possibly the organism(s) involved with the addition of up to 20 mM acetate.

Effect of Acetone on Dechlorination

While acetate was added as a potential carbon source to these cultures, the PCB was delivered in 0.1% (13.6 mM) acetone. Therefore, the potential exists for acetone to contribute to the metabolism of the microbial community by serving as an additional carbon source and to serve as an electron donor for dechlorination. Examination of the contribution of acetone to dechlorination and growth of the organisms in the ortho culture revealed that acetone alone could not maintain comparable growth or sustain the dechlorination of 2,3,4,6-CB through sequential transfer versus cultures supplied with 5 mM acetate. Growth and dechlorination did initially occur in acetone-supplied (no acetate) cultures (similar to that seen in FIGS. 1 and 2). However, this activity eventually declined and was not transferable (FIGS. 5 and 6). Cultures supplied with and re-fed 5 mM acetate plus 13.6 mM acetone maintained growth and dechlorination activity similar to those cultures re-fed 5 mM acetate alone (data not shown). Based on these results, the contribution of acetone to the growth and dechlorinating activity of the ortho-dechlorinating microorganisms was considered insignificant.

The elimination of acetone as the carrier for the PCB was found to cause a complete loss of dechlorinating activity (data not shown). The removal of the acetone was accomplished by pipetting the solubilized PCB into the culture tube and allowing the acetone to evaporate before medium and inoculum were added to the tube. This process left the PCB as a film on the tube and possibly unavailable to the dechlorinating microorganisms.

Effect of Hydrogen on Dechlorination

Figure 7:
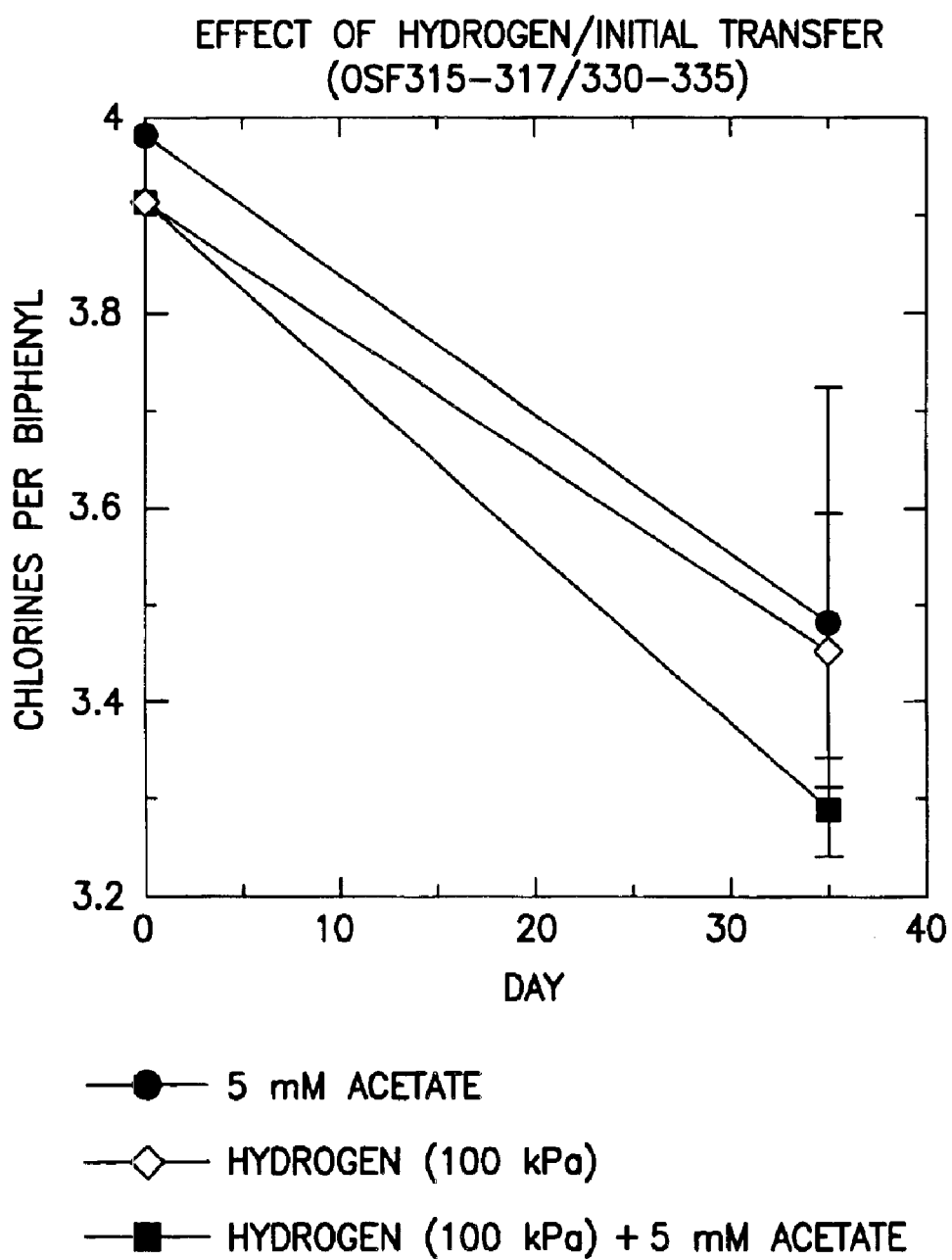
FIG. 7 is a graph of chlorines per biphenyl, as a function of time, and showing the effect of hydrogen and acetate on the dechlorination process.
Figure 8:
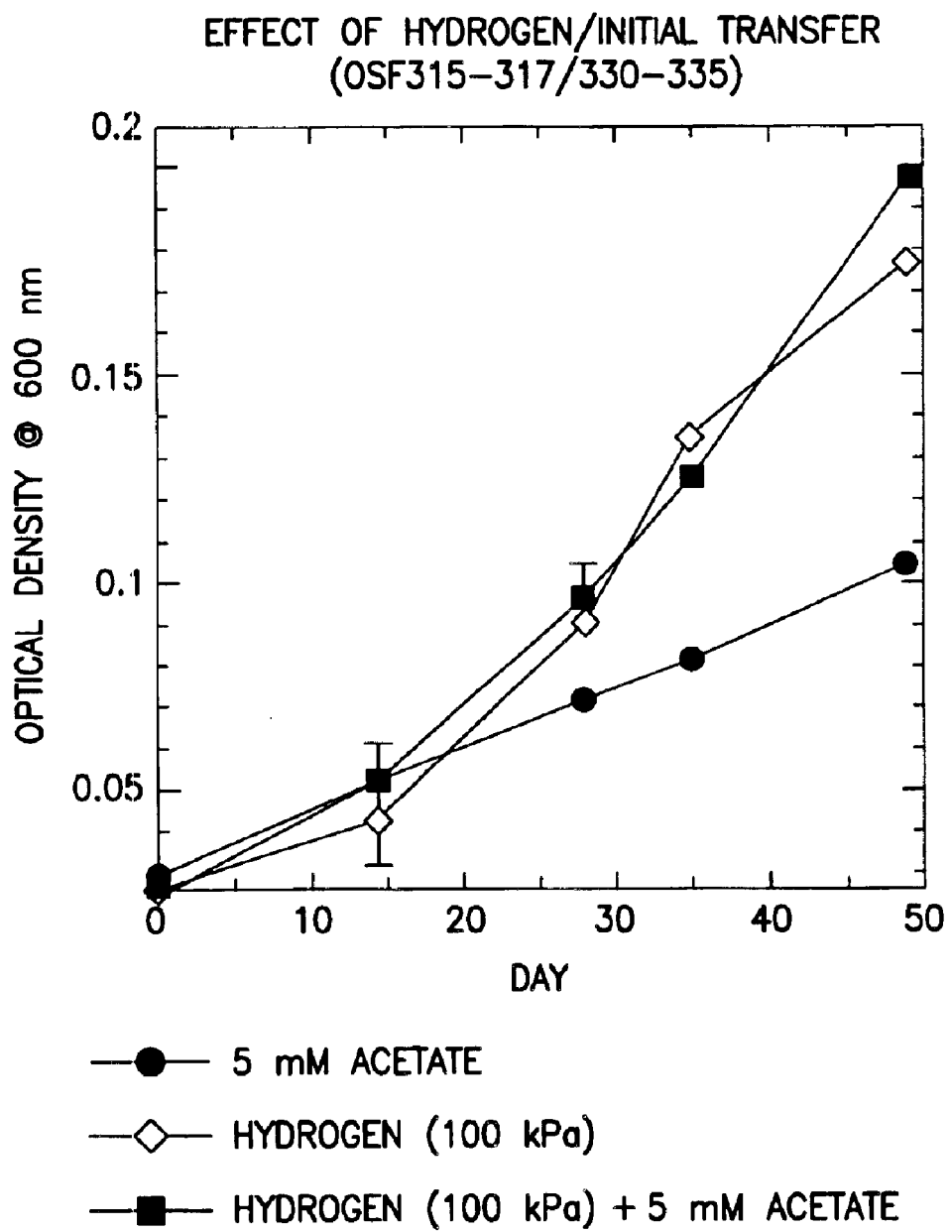
FIG. 8 is a graph of optical density of a dechlorination medium as a function of time, and showing the effect of hydrogen and acetate on the dechlorination process.
Figure 9:
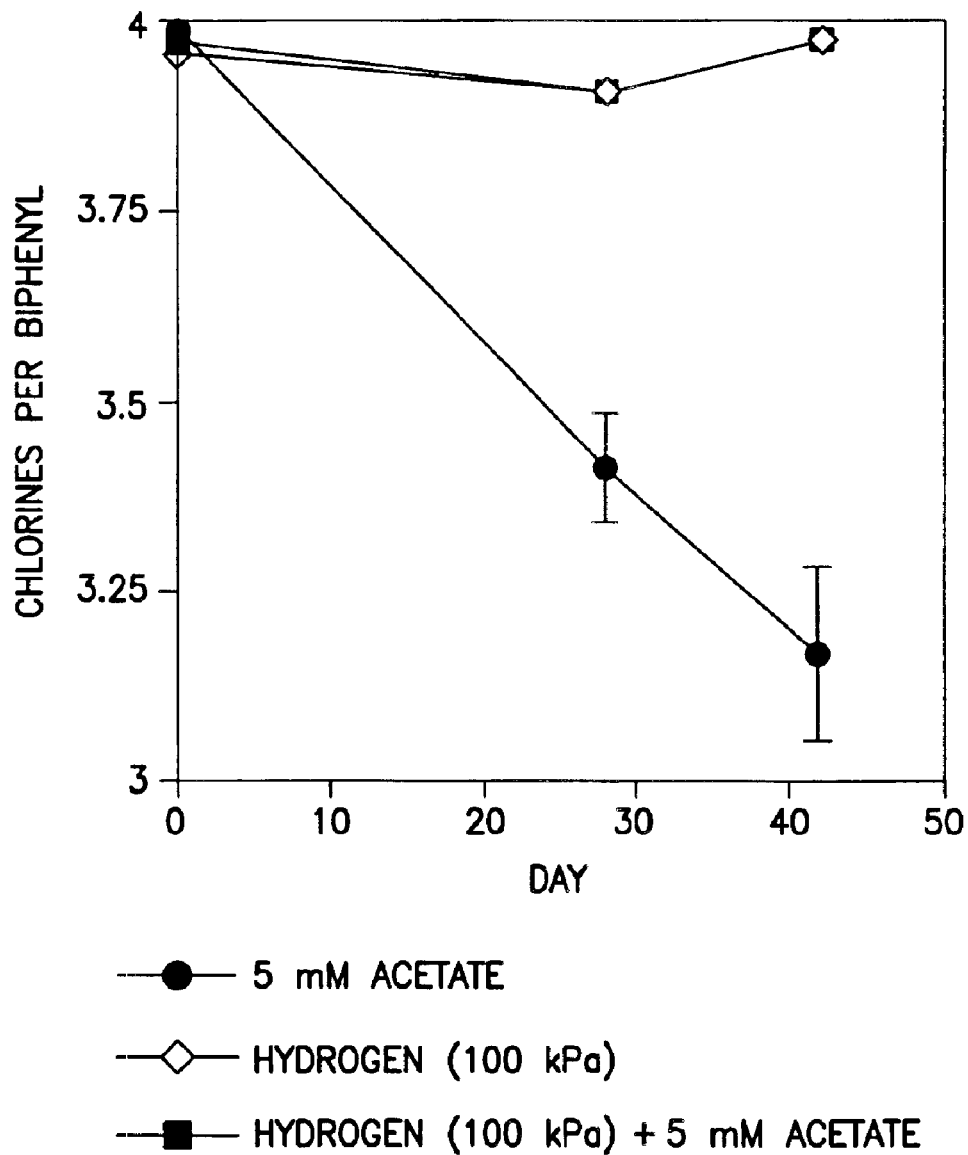
FIG. 9 is a graph of chlorines per biphenyl, as a function of time, and showing the effect of varying levels of hydrogen on the dechlorination process.
Figure 10:
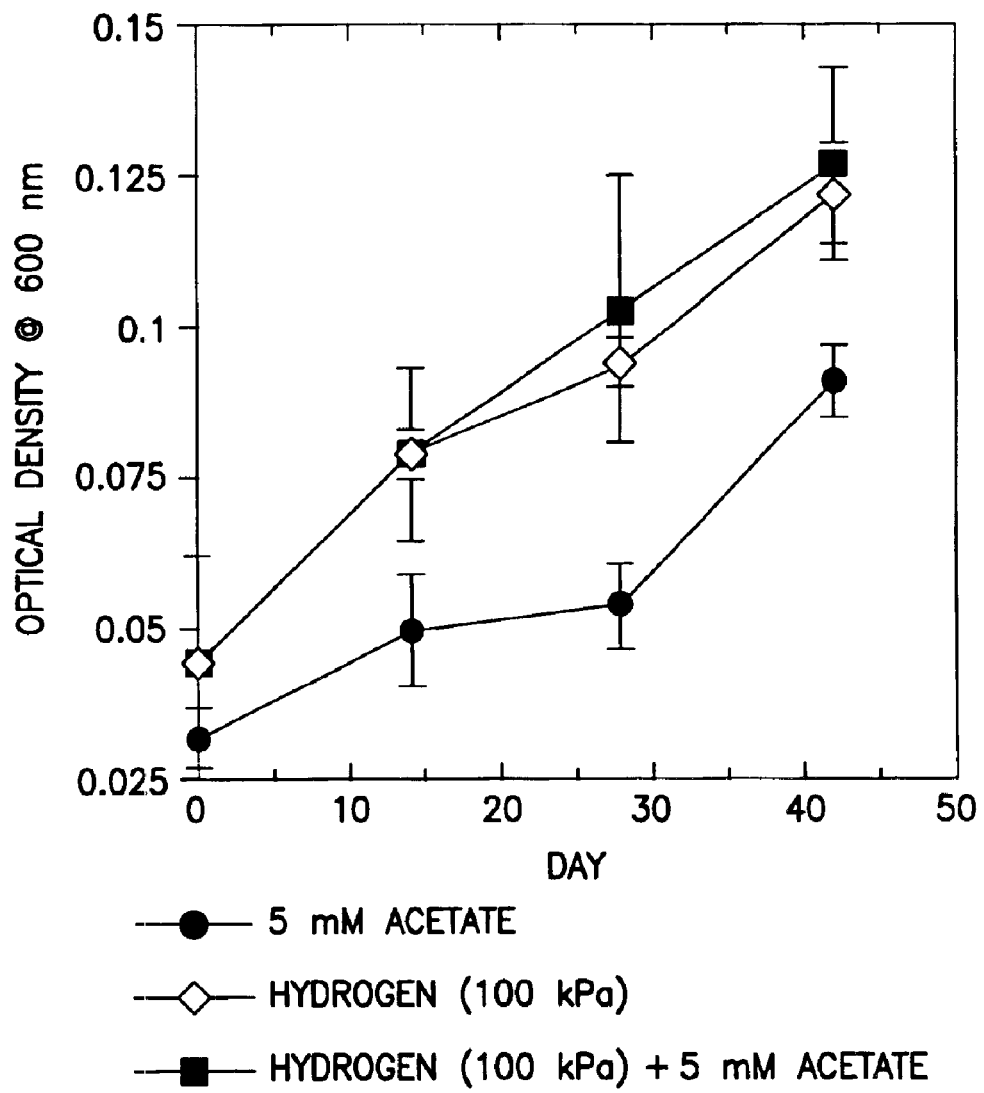
FIG. 10 is a graph of optical density of a dechlorination medium as a function of time, and showing the effect of varying levels of hydrogen on the dechlorination process.

The ortho culture was transferred from 5 mM acetate-fed cultures into fresh medium with $H_2:CO_2$ (80:20) at 100 kPa with no additional acetate. Dechlorination and growth continued initially in the cultures maintained with 100 kPa $H_2:CO_2$ (FIGS. 7 and 8). While the overall growth (based on changes in optical density) was greater with 100 kPa $H_2:CO_2$ than with 5 mM acetate alone, the dechlorinating activities in these cultures were similar to those of the acetate-fed cultures. Dechlorinating activity ceased following a second sequential transfer of the hydrogen-fed cultures into fresh medium with 100 kPa $H_2:CO_2$ and no acetate (FIG. 9). The same result was observed with cultures maintained with 100 kPa $H_2:CO_2$ and 5 mM acetate indicating an inhibitory effect resulting from the presence of the hydrogen on the dechlorinating activity (FIG. 9). Growth with hydrogen alone or with hydrogen and acetate continued at a rate faster than with acetate alone (FIG. 10). Sequential transfer of cultures amended with 10 mM formate resulted in a loss of growth as well as dechlorinating activity (data not shown). Methanogenesis continued in all of the 100 kPa hydrogen cultures (FIG. 11).

Tests were also made with cultures pressurized to 250 kPa of $H_2:CO_2$. Cultures under these conditions exhibited a decrease in the amount of PCB recovered during sampling with no dechlorination products detected in most cases versus the acetate-fed cultures (data not shown). Biphenyl was not detected in any of these cultures. These pressurized cultures all exhibited a coating on the tube with "crystal-like" structures. The same phenomenon was more pronounced after the second sequential transfer of the cultures maintained with 100 or 250 kPa $H_2:CO_2$, both with and without addition of acetate. This effect appeared to be mediated through the addition of hydrogen to these sediment-free enrichment cultures.

Methanogenesis and Ortho PCB Dechlorination

Figure 11:
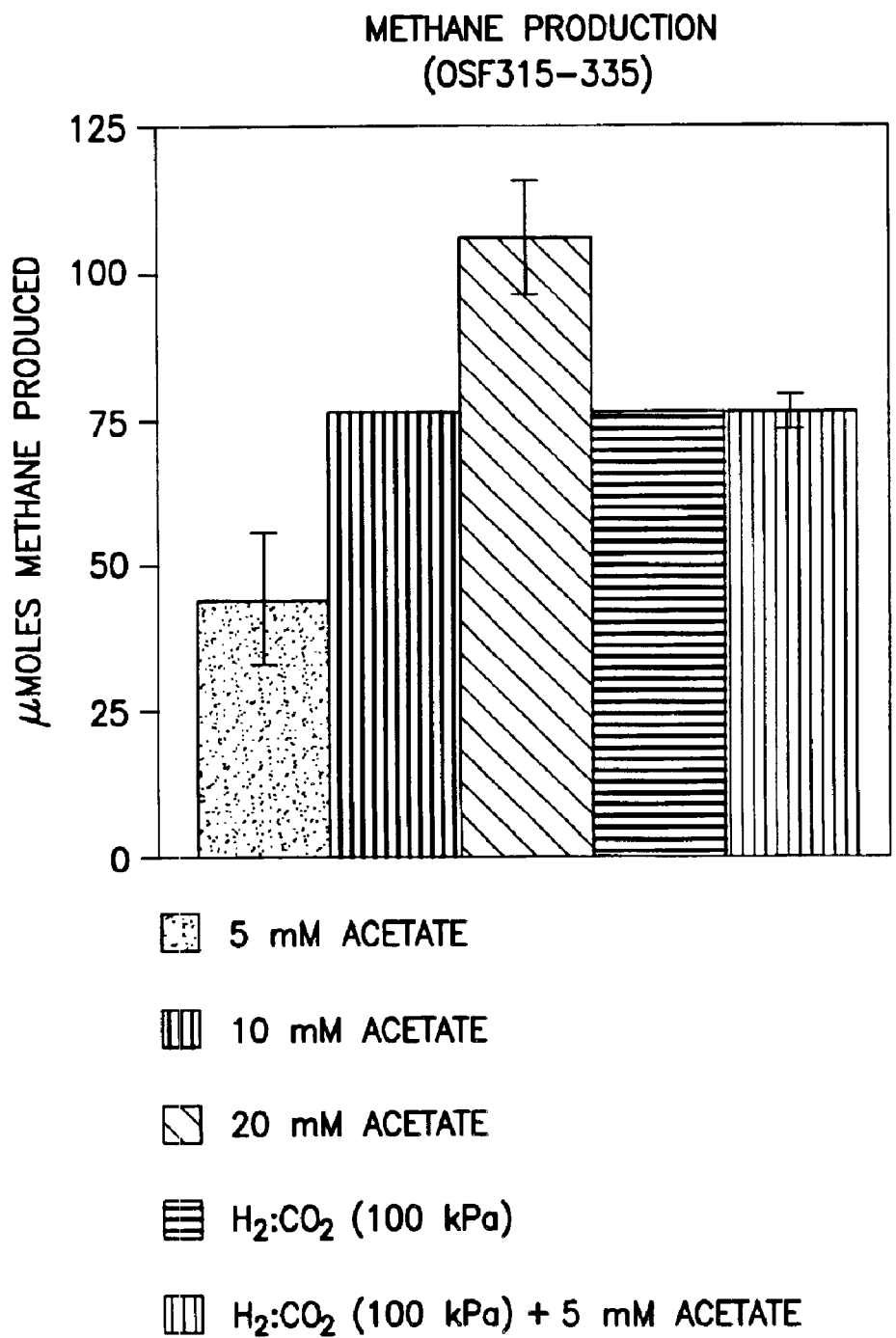
FIG. 11 is a graph of methane production for various dechlorination process conditions.

Methane levels in the cultures incubated with 5 mM acetate indicate that the majority of carbon in the cultures is going to methane production (FIG. 11). The cultures received 50 $\mu$moles of acetate at inoculation. For every mole of acetic acid consumed, one mole of methane is produced: $CH_3COO^- + H^+ + H_2O \rightarrow CH_4 + H^+ + HCO_3^-$. For every mole of acetic acid consumed, four times as many moles of chlorine can be removed through reductive dechlorination as represented by the following equation: $CH_3COO^- + H^+ + 4C_{12}H_6Cl_4 + 4H_2O \rightarrow 2HCO_3^- + 4C_{12}H_7Cl_3 + 4Cl^- + 6H^+$. The 5 $\mu$M acetate cultures (50 $\mu$M acetate per 10 ml culture) produced approximately 45 $\mu$moles of methane indicating that the majority of the $\mu$M acetate is going to methane. Although methane does not increase in equivalent molar amounts with the increase in acetate provided, the flow of electrons in the system in any case favors methane production and not PCB dechlorination. However, analysis of the 20 mM acetate cultures reveals that while 4 times the amount of acetate is provided in comparison to the 5 mM cultures, only slightly more than 2 times the amount of methane was produced. While methanogenesis still dominated electron flow, dechlorination was enhanced with 20 mM acetate indicating a shift of electrons toward reductive dechlorination (FIG. 3).

Initial testing of the sediment-free ortho culture amended with the 5 mM acetate with the same concentration of the methanogenic inhibitor BES (3 mM) used by Pulliam-Holoman et al. in experiments with the sediment-containing ortho PCB-dechlorinating cultures resulted in a complete loss of growth and dechlorinating activity (data not shown). Incubation of the sediment-free cultures amended with 5 mM acetate in the presence of BES at lower concentrations (0.1 to 1 mM) provided ambiguous results with dechlorination, growth and methanogenesis being inconsistent within a given set of conditions (data not shown). Dechlorination activity was not sustained in transfers in the presence of 1 mM BES alone.

Figure 12:
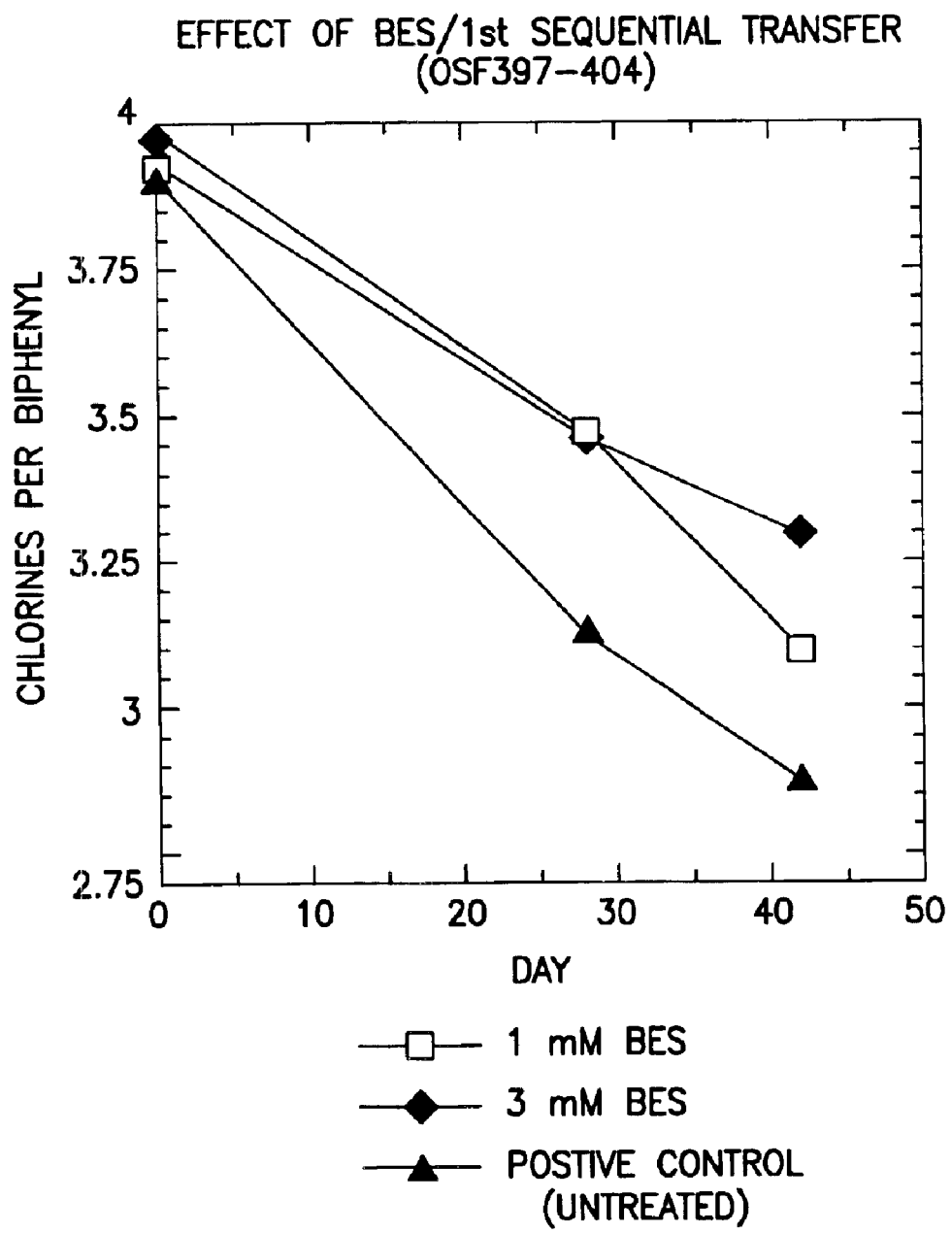
FIG. 12 is a graph of chlorines per biphenyl, as a function of time, and showing the effect of varying levels of BES on the dechlorination process.
Figure 13:
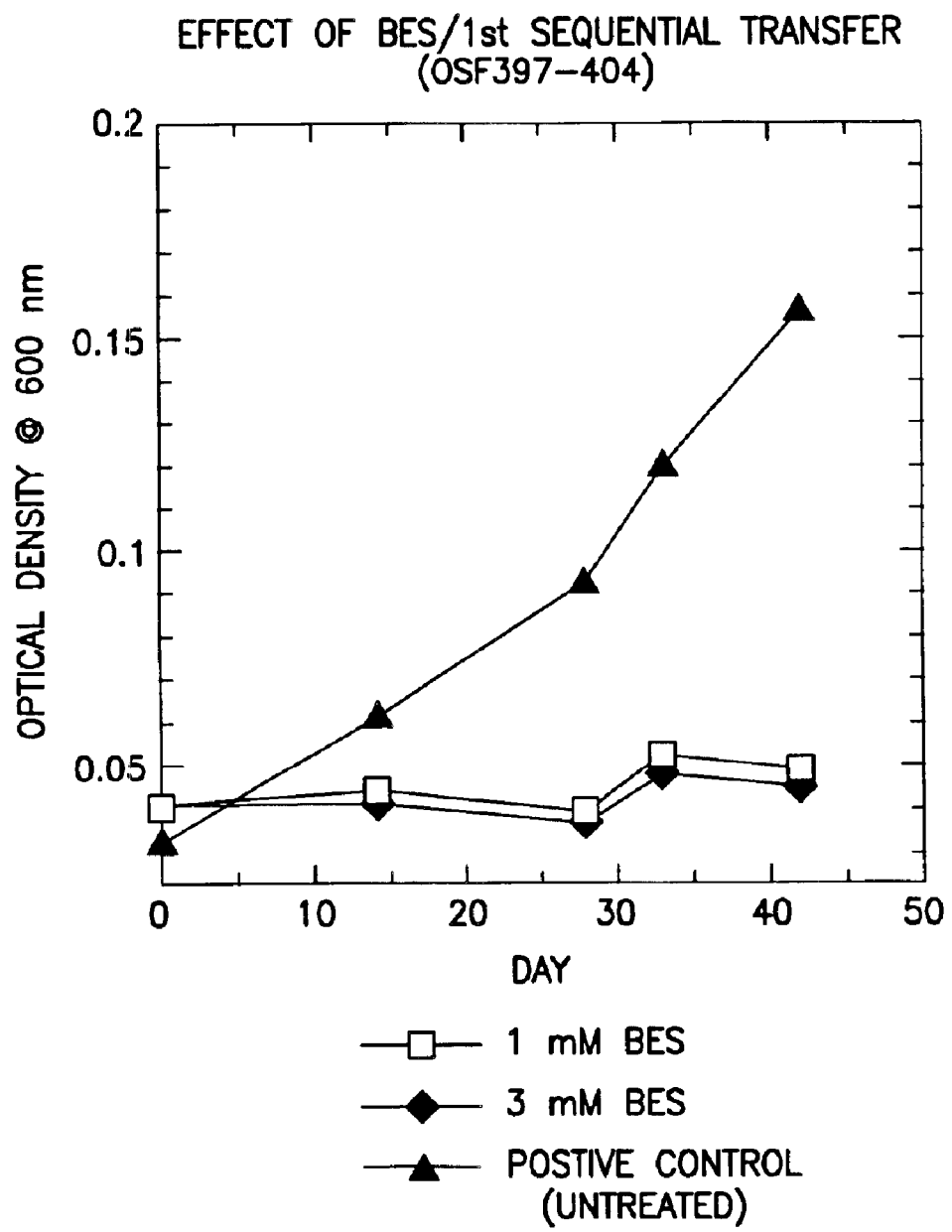
FIG. 13 is a graph of optical density of a dechlorination medium as a function of time, and showing the effect of varying levels of BES on the dechlorination process.

Based on the data indicating the stimulation of dechlorinating activity in cultures amended with 20 mM acetate, cultures amended with 5 mM acetate were transferred into medium containing 20 mM acetate and 1 to 3 mM BES. An extreme reduction in measurable optical density (OD) was observed while dechlorinating activity continued, albeit at a lesser rate than untreated cultures (FIGS. 12 and 13). No methane was detected in any of the BES-treated cultures. The only dechlorinating activity that was observed in the BES-amended cultures continued to be ortho dechlorination of 2,3,5,6-CB to 3,5-CB. Dechlorination was found to be transferable from BES-treated cultures into fresh medium amended with 20 mM acetate with no detectable methanogenesis (data not shown).

Microbial Community Structure of Enrichment Culture

Figure 14:
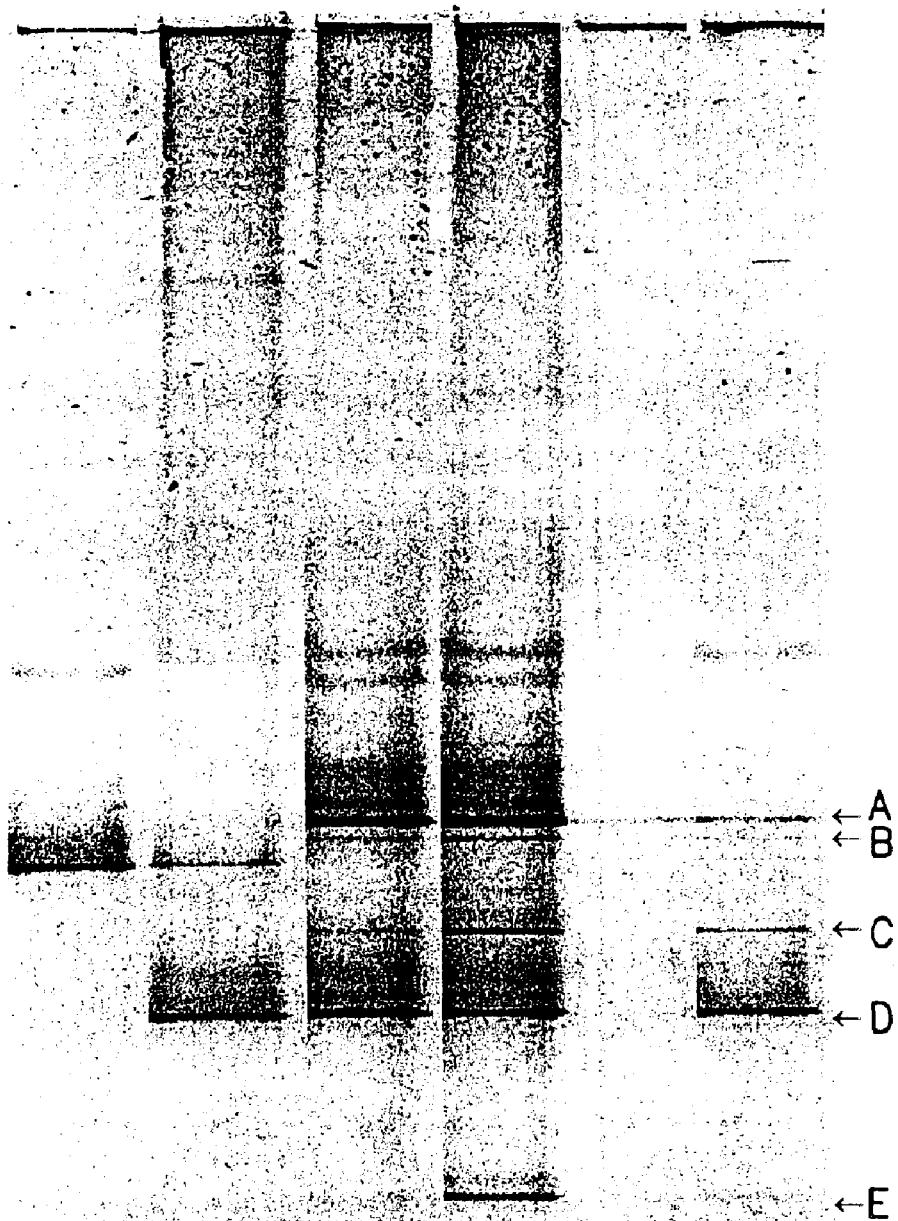
FIGS. 14 and 15 shows gels of 5 mM (FIG. 14) and 20 mM (FIG. 15) acetate-fed ortho cultures, showing the banding patterns thereof.
Figure 15:
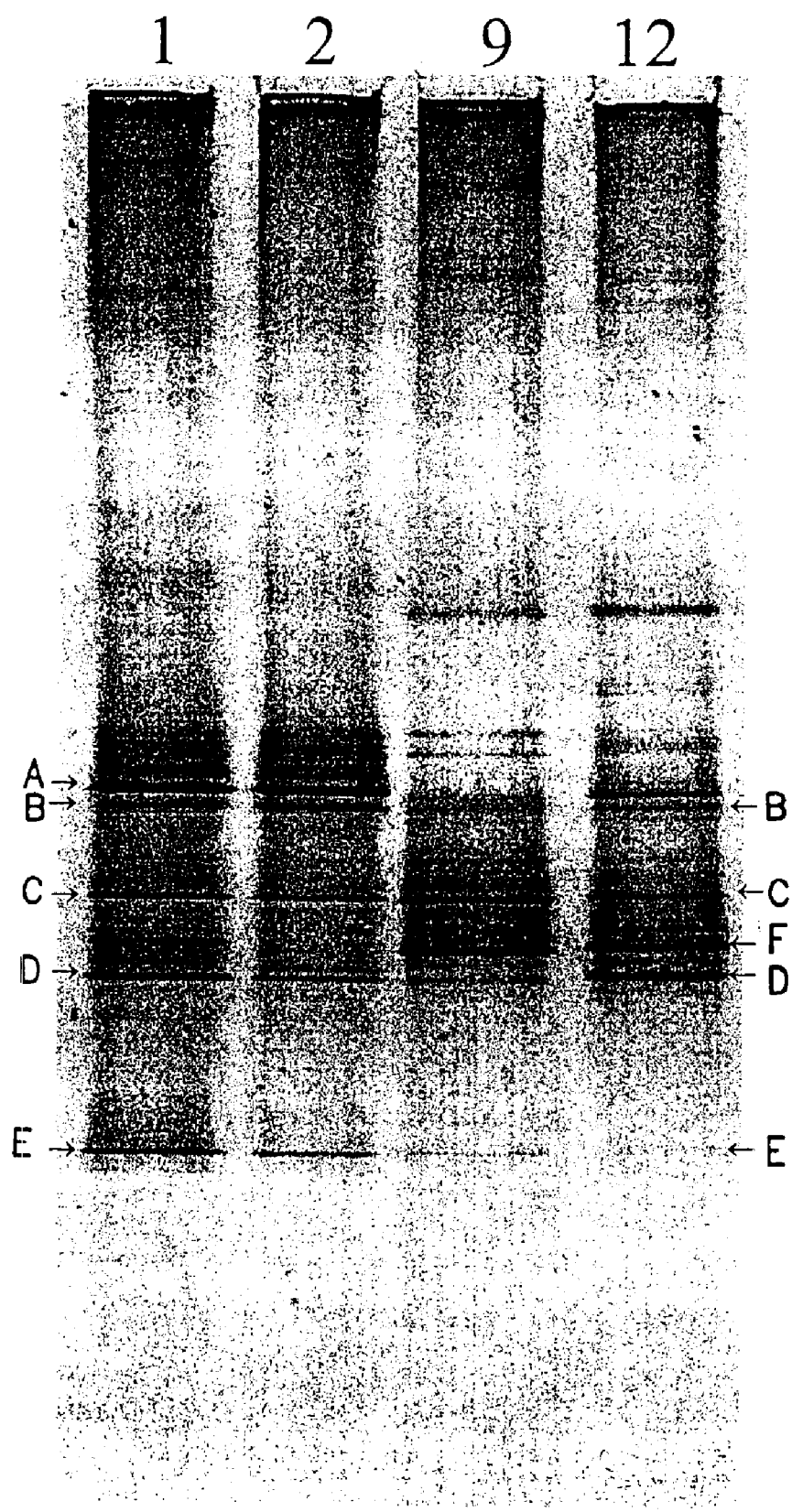

DGGE analysis of the community 16S rDNA was used to generate community profiles of the various enrichment cultures and to monitor the changes in the microbial population based on changes in enrichment conditions. As seen in FIGS. 14 and 15, the 5 and 20 mM acetate-fed ortho culture exhibited identical banding patterns with some differences in the intensity of the bands labeled B, D and E. A change in the microbial community was apparent when the 20 mM acetate-fed ortho culture was amended with 3 mM BES (FIG. 15). Band E was not detected and band C was not as intense in the BES-treated cultures as compared to the untreated cultures. As previously stated, the 20 mM acetate-fed cultures maintained dechlorinating activity in the presence of 3 mM BES (FIG. 12).

Changes in the community profile of the ortho culture were also observed in the cultures amended with $H_2:CO_2$, as compared to acetate-fed cultures. As stated above, cultures amended with $H_2:CO_2$, alone or in addition to 5 mM acetate, exhibited distinct changes in banding. Bands A, B and E were not visible or decreased in intensity in the presence of $H_2:CO_2$, with or without the additions of acetate. Band D also lessened in intensity when only $H_2:CO_2$ was present (no acetate). DGGE analysis of the microbial community also revealed the appearance of a distinct band (labeled F) only when the ortho culture was incubated with $H_2:CO_2$, Changes in the microbial community were also observed when cultures transferred in the absence of any added PCB were examined. Bands B, C and E lessened in intensity when the PCB was removed. The most significant change in banding intensity with the removal of the PCB was seen in Band A.

The most significant shift in the microbial community was observed when the microbial population of the ortho culture with and without acetate were compared. Transfer of the ortho culture in the absence of acetate resulted in a decrease in the number of visible bands as well as the intensity of those bands remaining. As stated above, transfers in the absence of acetate resulted in a complete loss of detectable growth and dechlorination.

Sequence Analysis

Bands excised from the DGGE gels for each of the culture conditions examined for microbial community profiles were sequenced. The closest relative was determined based on the partial 16S rDNA sequence from the excised bands. The results of the sequence analysis are shown in FIG. 22 (SEQ ID NO 1) and FIG. 23 (SEQ ID NO 2).

EXAMPLE 3

Materials and Methods for Development of Double-Flanked 2,3,4,5-CB Dechlorinating Consortium of Microorganisms Sediment Sample. Sediment samples were collected with a petite Ponar grab sampler at a subsurface depth of 4 meters in the Ashley River branch of Charleston Harbor (Charleston, S.C., USA). Sediments had a black coloration, and a gelatinous texture. The combined contents of the sampler were transferred to 0.95 liter canning jars (Ball Corporation, El Paso, Tex.). The jars were filled to the top and immediately sealed with dome tops and ring seals to exclude air. The samples were stored at ambient temperature in the dark prior to use.

Culture Procedures

An estuarine medium (E-Cl) was prepared as described by Berkaw et al., except that $Na_2SH_2O$ was not added. The final pH of the medium was 7.0. Charleston Harbor sediment, when used as a medium component during the initial enrichment development, was dried, ground and autoclaved twice for 1 hour at 121° C. for 30 minutes. Estuarine sediment from Charleston Harbor (2 ml) was obtained and inoculated into 8 ml E-Cl medium. Congener 2,3,4,5-CB, in 10 microliters of acetone, was added to the final concentration of 173 $\mu$l (50 ppm). Sediment was eliminated from the enriched consortia of microorganisms by sequential transfers of enrichment cultures into fresh medium. All cultures were incubated in the dark at 30° C.

The ensuing method is the same as that described for the ortho dechlorinating culture, with the following exceptions:

(1). Estuarine sediment from Charleston Harbor was substituted for estuarine sediment from Baltimore Harbor as inoculum;

(2) congener 2,3,4,5-CB was substituted for 2,3, 5,6-CB.

(3) sodium sulfide was not added to the medium.

(4) the dried Charleston Harbor sediment was added as a nutrient supplement instead of dried Baltimore Harbor sediment.

EXAMPLE 4

In this study three community analysis techniques, Amplified Ribosomal DNA Restriction Analysis (ARDRA), Denaturing Gradient Gel Electrophoresis (DGGE) and Terminal Restriction Fragment Length Polymorphism (TRFLP), were employed to examine a microbial community that reductively dechlorinates double flanked chlorines in 2,3,4,5-tetrachlorobiphenyl (2,3,4,5-CB). A rapid fingerprinting method was required to establish how microbial diversity changed in response to different culture conditions and to identify key species in the dechlorinating community by reductive analysis. The same primer set was used for DGGE and TRFLP analysis, allowing a direct comparison of these community-fingerprinting methods. To further validate this community analysis, a different primer set was used for the ARDRA analysis and the results compared for all three methods to determine similarities and differences.

In an attempt to identify the microbial catalysts involved in the dechlorination process, defined microbial communities have been developed by selective enrichment in minimal medium. Cutter et al. were able to enrich for a strictly ortho-dechlorinating community in a defined minimal medium sustained without the addition of sediment. Recently, a second sediment-free enrichment culture with the ability to dechlorinate doubly flanked chlorines was developed. These enrichment cultures contained microbial consortia in a completely defined environment, and as such provided an ideal experimental system for determining the efficacy of different microbial community analysis techniques.

Materials and Methods

Anaerobic enrichment cultures. A sediment-free estuarine medium (E-Cl) was prepared with the exclusion of $Na_2S.9H_2O$. The medium was autoclaved at 121° C. for 30 minutes and the final pH of the medium was 7.0. The enrichment cultures were prepared by inoculating sterile E-Cl with an active 2,3,4,5-CB para-dechlorinating culture. The congener 2,3,4,5-tetrachlorobiphenyl (CB) (AccuStandard, Inc., New Haven, Conn.) was solubilized in 10 $\mu$l of acetone and added to the enrichment cultures at a final concentration of 350 $\mu$M (100 ppm). Several combinations of energy sources and antibiotics were added to cultures, yielding five enrichment conditions, each in triplicate. The energy sources in the different treatments included fumarate (10 mM) and formate (10 mM). Hydrogen was also used as a substrate by substituting 101 kPA $H_2$—$CO_2$ (80–20 v/v) for $N_2$—$CO_2$ in the headspace. The antibiotics added were vancomycin and ampicillin, which were dissolved in deionized water, filter sterilized and added to final concentrations of 20 $\mu$g ml$^{-1}$. All cultures were incubated in the dark at 30° C.

Analytical techniques. PCBs were analyzed according to the method of Berkaw et al. Briefly, PCBs were extracted from enrichment culture samples with ethyl acetate (high-performance liquid chromatography grade, Fisher Scientific, Pittsburgh, Pa.) and the organic fraction was passed through a Florisil-copper column. PCBs were analyzed using a Hewlett-Packard 5890 series II gas chromatography (GC) equipped with a RTX-1 capillary column (30 m by 0.25 mm [I.D.] by 0.25 $\mu$m; Restek Corp., Bellefonte, Pa.) and a $Ni_{63}$ electron capture detector (ECD) as described previously. Individual PCB congeners were identified by matching the GC retention times with those of authentic standards (99% purity, AccuStandard) and quantified with a 16-point calibration curve for each congener.

Extraction of genomic DNA. DNA was extracted according to the procedure described previously. Briefly, 1 ml aliquots of culture samples were subjected to bead beating and phenol chloroform extractions followed by purification electrophoresis in a 1.3% low-melt agarose gel containing 2% soluble polyvinylpyrrolidone. The chromosomal DNA was excised from the gel and recovered with a Promega Wizard PCR Prep Kit (Promega, Madison, Wis.), according to manufacturers instructions.

ARDRA. Amplification of bacterial 16S rDNA from the mixed microbial community was carried out using the universal the universal primer set 519F (5'-CAG CA/CG CCG CGG TAA TA/TC-3') (SEQ ID NO.6) and 1406R (5'-ACG GGC GGT GTG TA/GC-3') (SEQ ID NO. 7) (12). The PCR reactions were preformed by using the GeneAmp PCR kit with Taq DNA polymerase (PE Applied Biosystems, Foster City, Calif.) in a PTC200 thermal cycler (MJ Research, Watertown, Mass.). The PCR reaction had the following cycle parameters: an initial denaturation step of 1.5 min at 94° C., followed by 30 cycles of denaturation for 30 s at 94° C., annealing for 30 s at 55° C., elongation 30 s at 72° C., with a final extension step of 5 min at 72° C. PCR products were checked for correct size and yield on a 0.8% TAE agarose gel (Fisher Biotech, NJ.). Triplicate PCR products were combined and purified using the QIAquick PCR purification kit (Qiagen, Valencia, Calif.). Plasmid libraries were generated in pCR2. 1 vector (Invitrogen. Carlsbad, Calif.) according to manufacturer's instructions and screened by restriction analysis after digestion with the endonucleases Hae III and Hha I (19).

Sequencing and Analysis. Two representative clones from each unique RFLP pattern were sequenced and analyzed using comparative phylogenetic analysis. A Qiagen Plasmid Mini Kit (Qiagen, Valencia, Calif.) was used to purify plasmid DNA according to manufacturer's instructions. The purified plasmid was used as the template for dye terminator cycle sequencing on an ABI 373 Automated sequencer (PE Applied Biosystems, Foster City, Calif.). The sequence was examined for errors and edited using DNAman (Lynnon BioSoft, Quebec, Canada), then checked for chimera formation using the Check_Chimera program of the Ribosomal Database Project. The sequence was then submitted to the National Center for Biotechnology Information's (NCBI) Basic Local Alignment Search Tool (BLAST) and the Ribosomal Database Project to determine percentage similarity with other 16S rDNA molecules.

TRFLP. For TRFLP analysis the primer set consisted of 314F (5'-CCT ACG GGA GGC AGC AG- 3') (SFQ ID NO. 8) and 534R (5'-ATT ACC GCG GCT GCT GG- 3') (SEQ ID NO. 9) yielding a 220bp fragment. Primer 3 14F had a fluorescent label (6-FAM) attached to the 5' end (Operon Technologies, Alameda, Calif.). PCR reactions were carried out using the program described above. Triplicate PCR products were combined and purified using a PCR purification kit (Qiagen, Valencia, Calif.). The purified PCR products (5 $\mu$l) were added to 10 U of restriction endonuclease, 1 $\mu$l of the appropriate buffer and made up to 10 $\mu$l with dH$_2$O. The samples were digested separately with the endonucleases, HaeIII and HhaI (New England Biolabs, Inc., Beverly, Mass.) at 37° C. for 6 h. Digested PCR product (2 $\mu$l) was added to 0.5 $\mu$l GeneScan 2500 TAMRA size standard and made up to 16 $\mu$l with ultra pure deionized formamide (Fisher Biotech, NJ). Each TRFLP analysis was performed in triplicate on an ABI 310 automated sequencer (PE Applied Biosystems, Foster City, Calif.). Controls consisted of formamide and size standard with and without the addition of restriction endonuclease and the respective buffers without PCR product addition. All samples were electrophoresed for 35 min in POP4 resin with a 15 s injection time. These data were analyzed using the GeneScan 3.1 software (PE Applied Biosystems, Foster City, Calif.).

DGGE. The PCR products generated for DGGE analysis were the same as the TRFLP-PCR fragments, however, the forward primer was modified to contain a 40 base GC-clamp (17) (Genosys Biotechnologies, Texas). Analysis of 16S rRNA PCR products by DGGE was performed as described by Muyzer et al., using the D-Code Universal Mutation Detection System (Bio-Rad, Hercules, Calif.). Combined triplicate PCR products were applied directly to 6% (wt/vol) polyacrylamide gels that contained a 20–80% gradient and electrophoresed for 17 h in 1×TAE buffer at a constant voltage of 50 V. After electrophoresis the gels were stained with Sybr-Green I DNA stain (Molecular Bio-Probes, Eugene, Oreg.) and the image was recorded using a fluoroimager (Molecular Dynamics, Sunnyvale, Calif.). To excise DNA fragments the gels were stained with ethidium bromide (0.5 $\mu$g ml$^{-1}$) and visualized using an UV transiluminator. Excised DNA fragments were obtained from one replicate for each enrichment culture treatment to ensure that all bands with the same migration distance represented the same ribotype. The DNA fragments were sequenced according to the method of Ferris et al. using a ABI 373 Automated sequencer (PE Applied Biosystems, Foster City, Calif.).

Diversity Indices. Sorenson's similarity coefficient was used as a diversity index for comparisons between DGGE and TRFLP. If an index of 1 was obtained the samples were considered identical while 0 indicated that the samples had no similarity. The Shannon-Weiner (H') diversity index was used to examine RFLP analysis of clone libraries.

Nucleotide sequence accession numbers. Sequences of the partial 16S rDNA of RFLP types 6, 26, 49, 181, 182, 187, 191, 194, 287, 412, 413, 414, 415, 419, 420, 421, 423, 426, 427, 428 were submitted to GenBank under accession no. AF295740 to AF295760 respectively. RFLP type 1 had been previously submitted to GenBank with accession number AF058000. Partial 16S rDNA sequences from the DGGE bands 1–4 were also submitted to GenBank under accession no. AF299353 to AF299356 respectively.

Results

Figure 24:
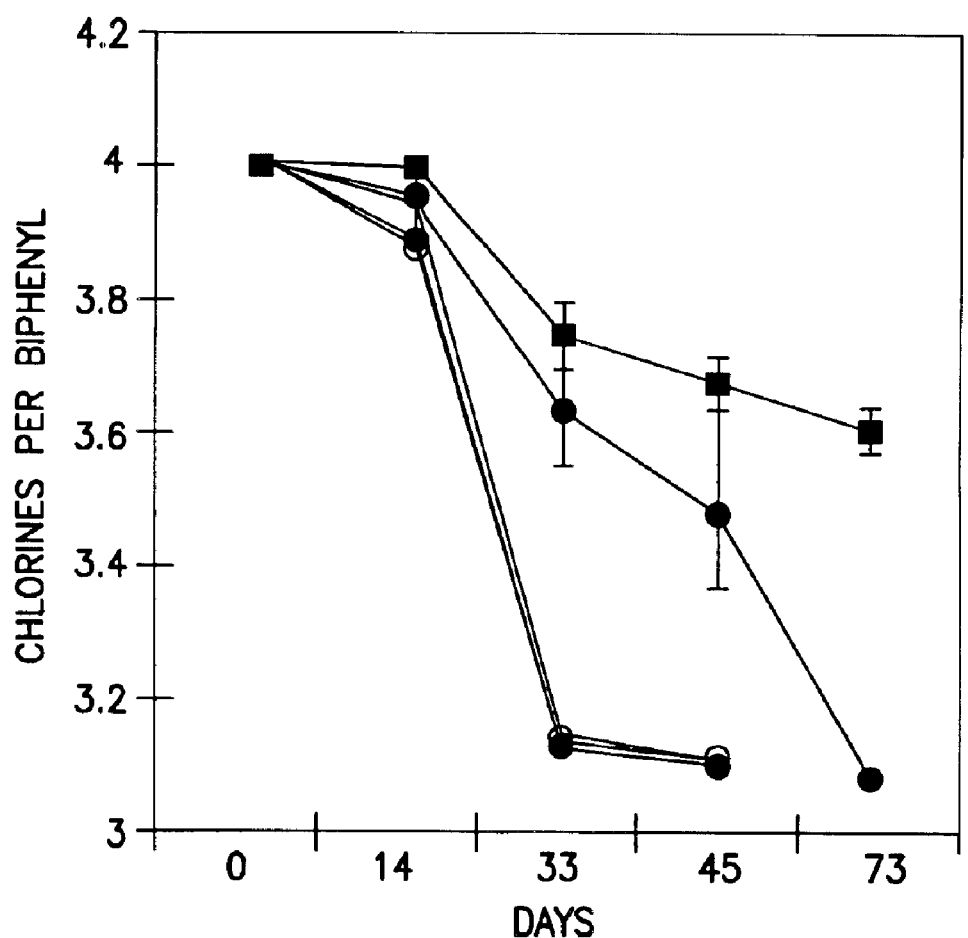
FIG. 24. Chlorines per biphenyl in 2,3,4,5-CB para-dechlorinating culture after incubation with E-C1 medium and 350 $\mu$M (100 ppm) 2,3,4,5-CB, (-○-) 10 mM Sodium Formate, (-♦-) 10 mM Formate & 20 $\mu$g ml$^{-1}$ Vancomycin, (-●-) 10 mM Sodium Formate & 20 $\mu$g ml$^{-1}$ Ampicillin, (-■-) 10 mM Sodium Fumarate and (-▲-) 100 kPa $H_2:CO_2$. Error bars represent the standard deviation of three replicates for each treatment.

Dechlorination activity of selective enrichment cultures. Anaerobic dechlorination rates monitored over 73 days in the enrichment cultures were highly reproducible for replicates of each culture treatment (FIG. 24). Formate and hydrogen-enriched cultures exchibited the most rapid dechlorination rates, with the fastest dechlorination occurring between days 14 and 33. When ampicillin was added to the formate culture dechlorination rates were reduced. However, over a longer time period the ampicillin-treated cultures eventually achieved the same level of dechlorination as the formate-only cultures. The addition of vancomycin to the formate culture did not cause a reduction in the dechlorination rate.

Figure 25:
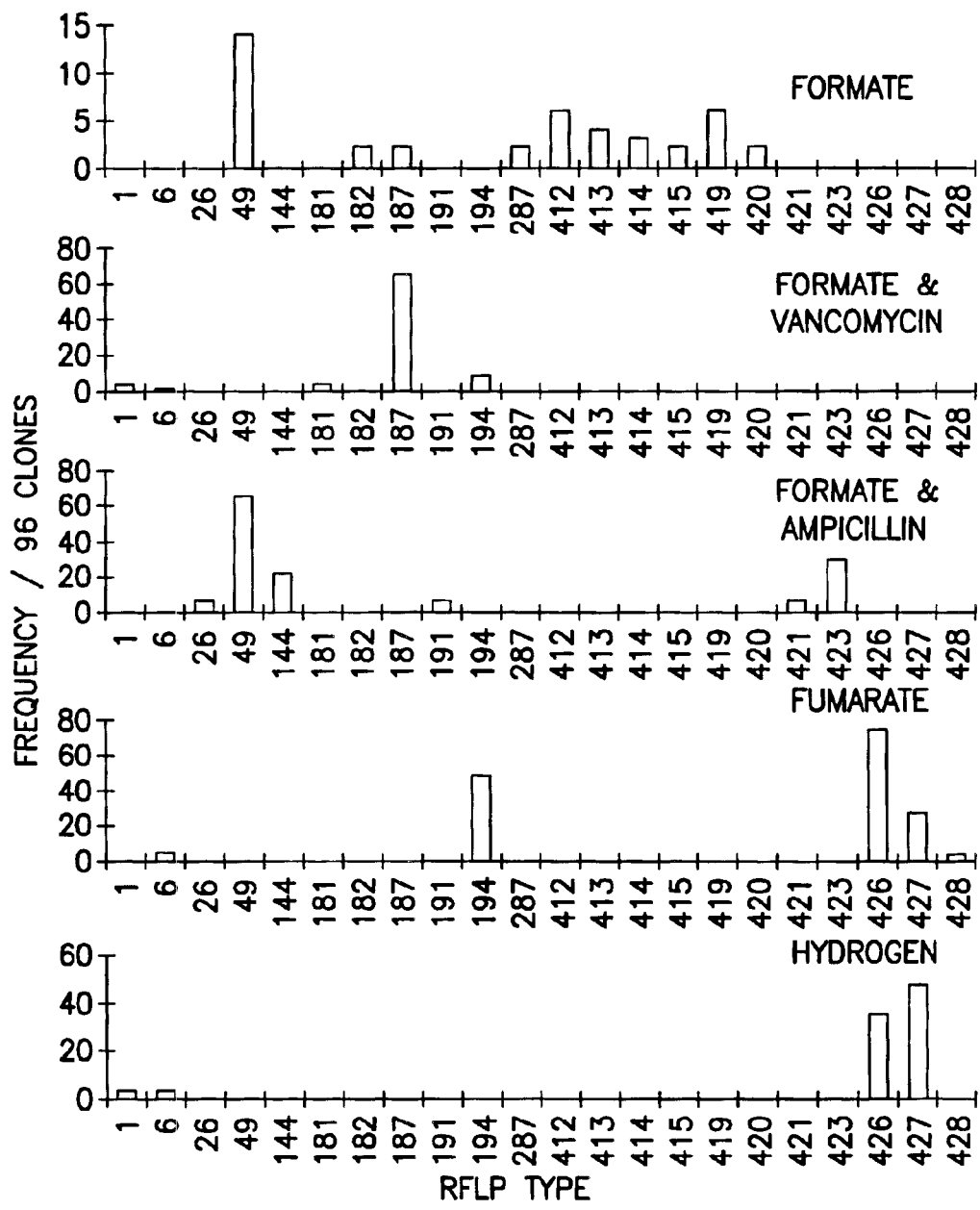
FIG. 25. Effects of different antibiotics and energy sources on community profiles from bacterial 16S clones. Each panel represents the frequency of each RFLP type from a random selection of 96 clones from a plasmid library. Panel A=10 mM Formate, B=10 mM Formate and Vancomycin 20 $\mu$g ml$^{-1}$, C=10 mM Formate and Ampicillin 20 $\mu$g ml$^{-1}$, D=10 mM Fumarate, E=Hydrogen. Frequency scale varies between profiles.

Fumarate-enriched cultures had the lowest rates of dechlorination over the 73 day time period. The effect of energy substrate on community profiles. Changes were detected in the microbial community profiles when enrichment cultures were transferred to media containing different energy sources (FIG. 25). Using ARDRA analysis it was determined that the formate-based culture contained the highest diversity of RFLP types and cultures that were enriched with fumarate or hydrogen had lower levels of RFLP diversity. Sequence analysis of the predominant RFLP types in the community had high similarities to species within three phylogenetic groups that included low G+C Gram positive eubacteria, δ proteobacteria and green nonsulfur eubacteria.

Figure 26:
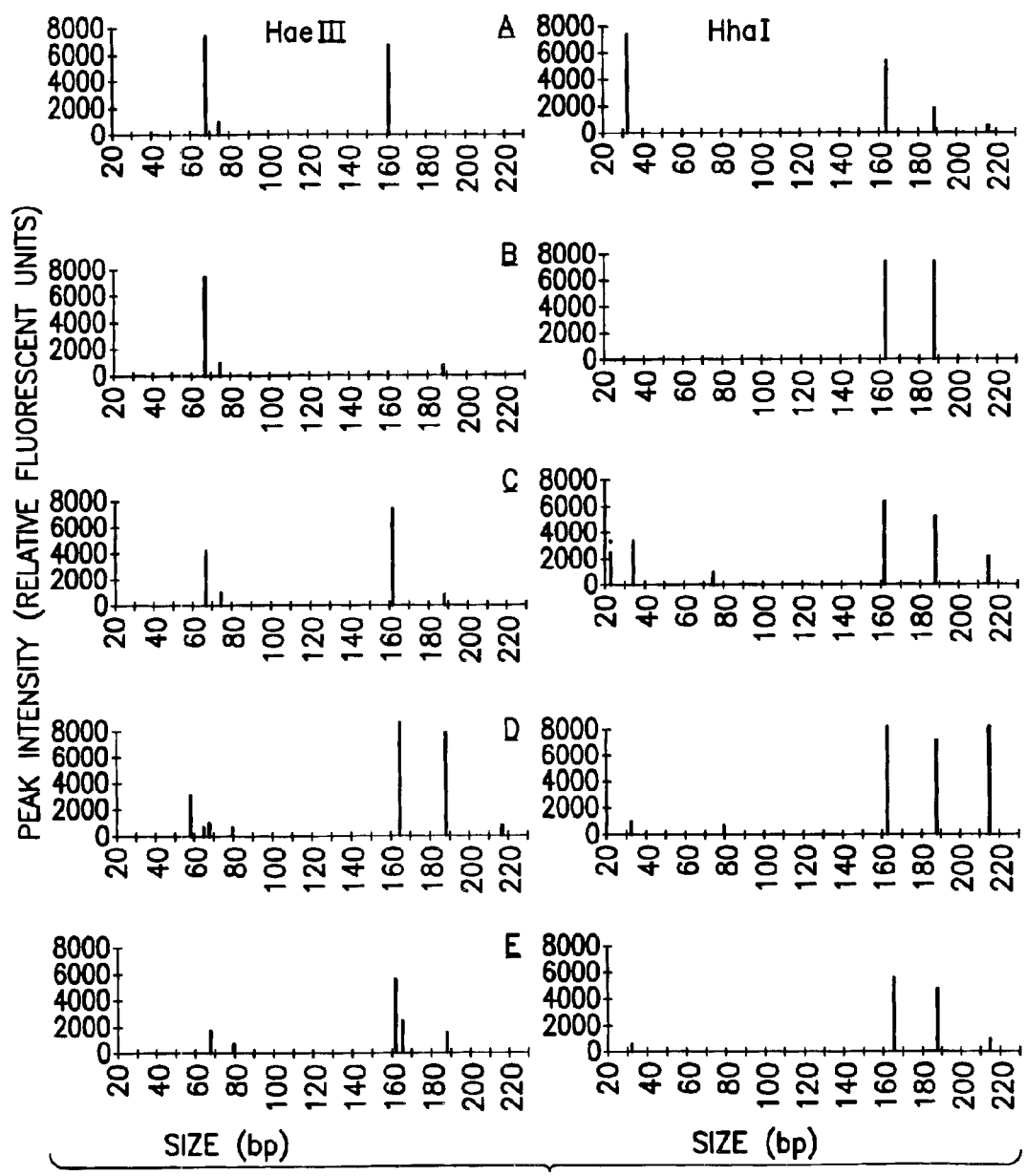
FIG. 26. TRFLP community profiles of 2,3,4,5-CB para-dechlorinating cultures treated with different antibiotics and energy sources. The left panel column contains the Hae III digestion patters; the right panel column contains Hha I. Panel A=10 mM Formate, B=10 mM Formate and Vancomycin 20 $\mu$g ml$^{-1}$, C=10 mM Formate and Ampicillin 20 $\mu$g ml$^{-1}$, D=10 mM Fumarate, E—Hydrogen.

TRFLP analysis indicated that different energy sources did not greatly alter microbial community diversity (FIG. 26). The formate cultures appeared to be dominated by two terminal fragments with three other fragments present at low relative levels. When compared with fumarate cultures the same terminal fragments were present, however, their relative intensities had changed. The hydrogen-enriched cultures were very similar to the formate cultures with the same terminal fragments present in both, although at different relative intensities. When comparing cultures developed with the three different energy sources by TRFLP no major community shifts were detected.

Figure 27:
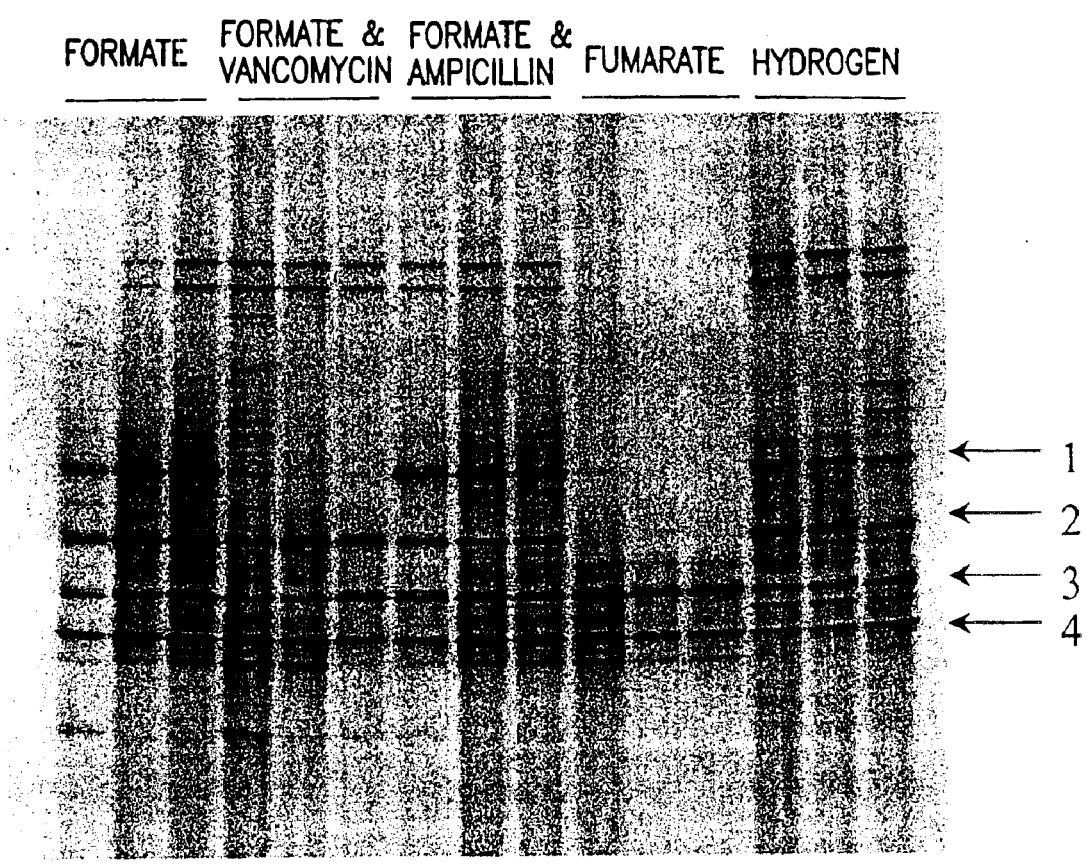
FIG. 27. DGGE analysis of 2,3,4,5-CB dechlorinating enrichment cultures. Each lane contains a PCR reaction performed on one of the replicate enrichment cultures for each treatment. Bands that were sequenced are labeled 1–4; band number 1 had the highest similarity in the GenBank database with an unidentified eubacterium (Accession no. AB015270) 98% similarity, number 2 had 91% similarity with an unidentified bacterial isolate (Accession no. U81649), number 3 had high similarity, 98%, with *Aminobacterium columbiense* (Accession no. AF069287) and band number 4 had 96% similarity with *Desulfovibrio* sp. BG50 (Accession no. U85475).

Examining the microbial community using DGGE it was apparent that four bands with the same relative migration distances were predominant in most of the cultures (FIG. 27). These four bands were sequenced to identify the microorganisms that they represented. Band number 1 had the highest similarity (98%) with an unidentified low G+C Gram positive eubacterium that had been isolated from deep sea sediment (Accession no. AB015270). The band designated number 2 had 91% similarity with an unidentified green non-sulfur eubacterium from an anaerobic digestor (Accession no. U81649). Band number 3 had high similarity (98%) with *Aminobacterium columbiense* (Accession no. AF069287) and band number 4 had 96% similarity with *Desulfovibrio* sp. BG50 that had been isolated from salt marsh sediment (Accession no. U85475). DGGE analysis had high levels of reproducibility between replicates, although, there were bands unique to different culture treatments that were detected at lower intensities. The fumarate culture was found to be the most unique when analyzed by DGGE with two of the dominant bands observed in the other cultures absent from the community profile. The hydrogen based culture profiles were similar to those with formate, exhibiting four major bands, although an additional band present lower in the gel was detected with greater intensity.

It could not be assumed that rDNA fragments with the same relative migration distance in different lanes of a DGGE gel represent the same microorganism. Chimera formation in the PCR and multiple ribosomal operons within individual species can potentially create multiple rDNA fragments for a single species. To overcome these factors, several rDNA fragments at the same position in the DGGE gel were sequenced to ensure that they each represented the same species. All were found to be of the same sequence. Therefore, in this study, the number of rDNA fragments on the DGGE gel were an indication of the species diversity present in the culture.

Effect of physiological inhibitors on the microbial community. ARDRA analysis indicated that the microbial community present in the enrichment cultures changed when treated with antibiotics. The 10 mM formate based culture contained the highest diversity of RFLP types (FIG. 25). Treatment of the culture with vancomycin resulted in the diversity being greately reduced with one dominant RFLP type (RFLP 187). Treatment with ampicillin also reduced the diversity of RFLP types, although the RFLP type 187, was absent from this profile. In contrast, RFLP type 49, which was non-detectable when treated with vancomycin, is dominant in the ampicillin-treated culture.

Examining the antibiotic treatment effects on the community using TRFLP indicated that the 10 mM formate culture (FIG. 26) contained more detectable terminal peaks relative to cultures grown with 10 mM formate and vancomycin. A similar reduction in peak diversity was observed after the 10 mM formate culture was treated with ampicillin. Various terminal peaks that were present in the untreated formate culture were not detectable after antibiotic treatment. This is probably due to the inhibition of certain species by the antibiotic. Examination by DGGE revealed that treatment of the formate culture with vancomycin resulted in the reduction or disappearance of one of the dominant bands (band number 1). Although three of the dominant bands remained, the vancomycin treatment resulted in more variability in the lesser intensity bands. This included the appearance of a more intense band in two out of three replicate cultures. The dominant bands within the formate cultures were not altered by the addition of ampicillin. However, changes can be detected in the less intense bands.

Phylogenetic similarities of RFLP types from enrichment cultures. Phylogenetic analysis of the predominant RFLP types led to the identification of species in the microbial community. A collection of the most commonly found RFLP types and their sequence similarities are shown in Table 1.

Table 1. Phylogenetic similarities of predominant RFLP types from PCB dechlorinating enrichments, based on bacterial 16S rRNA gene sequences. Phylogenetic affiliations include members of delta-sub-division of the proteobacteria (δ), low GC Gram positives (G+) and green non-sulfur bacteria (GNS).

| RFLP Type | Closest Phylogenetic Relative | % similarity to closest relative | Phylogenetic affiliation |
|---|---|---|---|
| 1 (AF) | *Thermotoga maritime* (M21774) | 87 | T |
| 6 (AF295760) | *Desulfuromonas palmitatis* (U28172) | 99 | δ |
| 26 (AF295746) | *Deulfothiovibrio peptidovorans* (U52817) | 98 | G+ |
| 49 (AF295759) | *Acetivibrio cellusolvens* (L35515) | 94 | G+ |
| 144 (AF295740) | Desulfovibrio sp. BG50 (U85475) | 98 | δ |
| 181 (AF295741) | Unidentified bacterium (AB015270) | 91 | G+ |
| 182 (AF295742) | *Desulfovibrio caledoniensis* (U53465) | 87 | δ |
| 187 (AF295743) | *Aminobacterium columbiense* (AF069287) | 97 | G+ |
| 191 (AF295744) | *Aminobacterium columbiense* (AF069287) | 97 | G+ |
| 194 (AF295745) | Unidentified bacterium (AB015270) | 97 | G+ |
| 287 (AF295747) | Unidentified eubacterium (AF058005) | 88 | GNS |
| 412 (AF295748) | Unidentified bacterium (AB015270) | 97 | G+ |
| 413 (AF295749) | *Desulfovibrio caledoniensis* (U53465) | 99 | δ |
| 414 (AF295750) | *Aminobacterium columbiense* (AF069287) | 95 | G+ |
| 415 (AF295751) | Unidentified bacterium (AB015270) | 94 | G+ |
| 419 (AF295752) | Unidentified bacterium (AB015270) | 92 | G+ |
| 420 (AF295753) | *Desulfovibrio caledoniensis* (U85475) | 99 | δ |
| 421 (AF295754) | Unidentified bacterium (AB015270) | 97 | G+ |
| 423 (AF295755) | Unidentified bacterium (AB015270) | 97 | G+ |
| 426 (AF295756) | *Aminobacterium columbiense* (AF069287) | 98 | G+ |
| 427 (AF295757) | *Desulfovibrio caledoniensis* (U53465) | 99 | δ |
| 428 (AF295758) | Unidentified eubacterium (U81643) | 93 | GNS |

Two phylogenetic groups, the δ-proteobacteria and the low G+C Gram-positive bacteria dominate the ARDRA profiles. There are a number of RFLP patterns with high similarities to Desulfovibrio species, which are Gram-negative anaerobic microorganisms with a respiratory type of metabolism often using sulfur compound as terminal electron acceptors. Another frequently detected 16S rDNA sequence had a high similarity to *Desulfothiovibrio* species, which is a low-GC Gram-positive thiosulfate-reducing microorganism that has been previously detected in corroded offshore wells. *Aminobacterium columbiense*, which is also in the low GC-Gram positive group, had high similarity values to a RFLP type detected in every culture in this study. This microorganism is an amino acid degrading obligate anaerobe that was previously isolated form anaerobic sludge. The cultures also contained RFLP types with highest sequence similarity to a number of as yet uncultured eubacteria. These included species from an anaerobic digestor fed with wine distillery waste and another microorganism, which has been detected in deep cold sediments.

Diversity indices for ARDRA and TRFLP community profiles. The diversity indices employed allowed the comparison of RFLP diversity for the different enrichment cultures (Table 2).

Table 2. Diversity indices were used to examine the RFLP distribution in the clone libraries from the 5 different enrichment cultures. S=total number of different RFLP types present in the clone library, H'=Shannon-Weiner function is based on the ability to predict individuals identity from a mixed community, a value of 0 indicates that all individuals are the same.

| CULTURE | S | H' |
|---|---|---|
| Formate | 17 | 2.47 |
| Formate and Vancomycin | 14 | 1.3 |
| Formate and Ampicillin | 10 | 1.59 |
| Fumarate | 4 | 0.89 |
| Hudrogen | 16 | 1.88 |

To examine the clone libraries the Simpson and Shannon-Weiner indices were used. These indices suggest that the 10 mM formate culture contained the most diverse microbial community, while the addition of the antibiotics ampicillin and vancomycin reduced diversity. The hydrogen enriched culture had relatively high levels of RFLP diversity, similar to the formate culture without antibiotic addition, while the 10 mM fumarate enriched cultures had very low detectable diversity.

To compare DGGE gel community patterns of the different enrichments the Sorenson's similarity coefficient was used (Table 3).

Table 3. Sorenson's similarity coefficient was used to compare the results from DGGE and TRFLP for different enrichment cultures, the samples can be considered as identical if a value of 1 was obtained, while a value of 0 indicates that the samples are completely different. The cultures conditions are A=Formate, B=Formate & Vancomycin, C=Formate & Ampicillin, D=Fumarate, E=Hydrogen.

| Cultures compared | DGGE | TRFLP |
|---|---|---|
| A & B | 0.92 | 0.83 |
| A & C | 0.83 | 0.93 |
| A & D | 0.55 | 0.63 |
| A & E | 0.83 | 0.8 |
| B & C | 0.91 | 0.77 |
| B & D | 0.60 | 0.57 |
| B & E | 0.66 | 0.62 |
| C & D | 0.66 | 0.71 |
| C & E | 0.73 | 0.75 |
| D & E | 0.4 | 0.47 |

The indices revealed that highest levels of similarity were found when comparing formate based cultures and the least community similarity was found when comparing formate, to hydrogen or fumarate based cultures. The Sorenson's index was also applied to TRFLP and the same trends found in DGGE were observed.

Discussion

Formate and hydrogen enriched cultures had reproducible and rapid rates of dechlorination. The reaction proceeds no further than 2,3,5-CB indicating that this microbial community attacks only the doubly flanked para-chlorine of 2,3,4,5-CB. As the dechlorinating rate with these two substrates was identical and formate hydrogenlyase is prevalent among anaerobes that metabolize hydrogen and formate (8), it is likely that the same species utilizes both substrates for reductive dechlorination. Cultures containing fumarate had a lower rate of dechlorination (125 days) here and in a previous report (23), which suggests that species in this microbial community are unable to use fumarate as effectively as formate or hydrogen for reductive dechlorination. The activity of the formate cultures was altered by treatment with antibiotics. In formate-based enrichments the addition of vancomycin did not reduce dechlorination although ampicillin addition resulted in a reduced rate. In a previous stud Wu et al. 2000 determined that 2,3,4,5-CB dechlorinating communities enriched with fumarate were only partially inhibited with vancomycin and completely inhibited with ampicillin. The dechlorinating bacteria within the fumarate-enriched cultures may be more susceptible to ampicillin and vancomycin because of their lower growth efficiency. Alternatively, if a co-culture with a fumarate oxidizing bacterium was required to generate $H_2$ as a substrate for the dechlorinating species, partial or complete inhibition of the first species in the pathway would affect the overall rate of dechlorination.

The molecular methods used in this study indicated that the microbial community profile changed in response to different energy sources. ARDRA indicated that the formate culture was the most diverse with 10 different predominant RFLP types. The hydrogen and fumarate cultures had less diversity than the formate cultures. The hydrogen and fumarate cultures had very similar patterns with several RFLP types in common. The profiles were dominated by two RFLP types: an *Aminobacterium* sp. And a *Desulfovibrio* sp. In contrast, both DGGE and TRFLP detected four predominant ribotypes, which appeared with all energy sources. The patterns were similar for all three communities, except in the fumarate culture in which two RFLP types were undetectable.

Addition of antibiotics to the formate cultures resulted in the detection of lower diversity by all of the molecular methods. This was confirmed by using Sorenson's similarity coefficient for the DGGE and TRFLP and Shannon-Weiner function for the ARDRA analysis. Several novel RFLP types were found in antibiotic treated cultures that were not detected in antibiotic free cultures. However, DGGE and TRFLP analysis revealed similar community patterns in both the treated and untreated formate cultures. In order to explain the discrepancy between the analytical methods, DNA of the predominant ARDRA library clone types and DGGE bands were sequenced and the phylogenetic identity of each was determined by comparative sequence analysis. Several RFLP types had equivalent similarity values to 16S rDNA sequence of the same species and these had high similarity values to one another (>99% for *Desulfovibrio* sp. And >98% for *Aminobacterium* sp.). When RFLP types with high similarity values were combined, the ARDRA community consisted of four predominant RFLP types with high similarity to the four predominate DNA fragments detected by DGGE. These results indicate that ARDRA differentiated highly similar rDNA sequences consistent with multiple genomic copies, strain variation or PCR error. TRFLP and ARDRA are both based upon restriction analysis. However, TRFLP is less sensitive to small differences in the DNA due to the shorter size of the DNA fragment (230 bp compared to 887 bp for the ARDRA) and only the terminal fragment is examined in this analysis. DGGE analysis is theoretically capable of detecting single base changes with the correct optimized gradient, but the denaturing gradient used in this study was optimized for differentiation of the total community. Therefore, 16S rDNA sequences with slight (3 to 4 bp) differences within the 230 bp PCR generated fragment grouped together in the same band as a result of the wide gradient. After correcting ARDRA analysis for sensitivity, 4 predominant rDNA sequences were observed regardless of the method (ARDRA, TRFLP, DGGE) or primers used.

Formate- and hydrogen-grown cultures had very similar DGGE profiles. Although the hydrogen-grown culture had several additional bands, the predominant ribotypes in both cultures consisted of the G+C Gram positive eubacterium (band 1), the green non-sulfur eubacterium (band 2), *Aminobacterium* sp. (band 3) and the *Desulfovibrio* sp. (band 4). Growth with fumarate resulted in detection of only the *Aminobacterium* sp. (band 3) and the *Desulfovibrio* sp. (band 4). Since the rate of dechlorination was reduced in this culture, and the G+C Gram positive eubacterium (band 1) and green non-sulfur eubacterium (band 2) are not detectable, these species may be associated with reductive dechlorination. In contrast the *Aminobacterium* sp. (band 3) and the *Desulfovibrio* sp. (band 4) we present with similar relative intensities in all treatments, including the slower dechlorinating fumarate. One explanation for their ubiquity is that Aminobacterium sp. and possibly the low G+C Gram positive eubacterium, which have high 16S rDNA similarity to clostridia, may grow on amino acids such as cysteine which is added to the medium as a sulfur source and reductant (4). *Desulfovibrio* sp. may use formate, hydrogen or fumarate as electron donors with partially oxidized sulfide generated from cysteine as an election acceptor for growth.

Using DGGE and ARDRA to identify microorganisms present in the enrichment treatments yielded the same predominant species groups, but differences were found when trying to identify strains. These differences in sensitivity are probably a result of different primers and limitations inherent in the ARDRA process. Biases associated with clone library construction and random selection of clones for restriction analysis will affect the representation of the microbial community. Also individual species can have a number of genomic 16S rRNA genes, which may result in higher numbers of that microorganism being detected in the 16S rRNA library. Although the ARDRA and DGGE techniques used different primer sets, the methods still identified the same predominant species of microorganisms in the enrichment cultures. The agreement between the methods using different primer sets indicates that PCR bias did not affect the apparent community diversity in this study.

DGGE and TRFLP had similar community profiles of predominant DNA fragments. Microbial species could be putatively assigned to specific TRFLP peaks by reductive analysis of DGGE and TRFLP profiles, which confirmed the detection or absence of species under different growth treatments. Although TRFLP generally corroborated DGGE analysis of the diversity, the inability to confirm ribotype assignments by comparative sequence analysis limits the usefulness of this technique for reductive analysis and identification of a putative PCB dechlorinator. In the DGGE analysis there were a few bands present at low intensity which may have not been detected by TRFLP due to an arbitrary cut-off point, which was assigned at 50 fluorescent units. This cut-off value may have removed from detection a number of terminal fragments that represent lower frequency species in the community.

A highly enriched community of bacteria that reductively dechlorinate the flanked chlorine(s) of 2,3,4,5-CB were examined in the absence of isolation by ARDRA, TRFLP and DGGE. Although ARDRA was previously effective for identifying phylogenetic groups that were associated with the activity in a highly diverse 2,3,5,6-CB ortho-dechlorinating community in the presence of sediments (19) results herein show that this method is too sensitive for analysis of a highly defined, low diversity community enriched in sediment-free defined medium. DGGE, which is ineffective for highly diverse communities, was most effective for analyzing this low diversity culture. TRFLP corroborated the DGGE analysis and was effective for monitoring changes that occur as a result of culture treatment, but could not be used for comparative analysis of species in the cultures. Results of this study show that species associated with dechlorination of 2,3,4,5-CB could be identified by reductive analysis of DGGE generated community profiles of these highly enriched communities after growth with different energy sources and antibiotic treatments. Phylogenetic groups associated with double-flanked dechlorination of 2,3,4,5-CB, low G+C Gram positive, Desulfovibrio sp. and green non-sulfur eubacteria, were also the predominate phylogenetic groups previously reported to be associated with ortho-dechlorination of 2,3,5,6-CB. Herein we have demonstrated that this reductive approach of monitoring dechlorination after selective inhibition of individual species can be used to identify potential catalysts from environmental communities without isolation. This approach is currently being used to enrich for individual species and confirm the role of each species in the reductive dechlorination of 2,3,4,5-CB by this microbial community.

The disclosures of all references cited herein, including the references identified in the ensuing bibliography, are hereby incorporated herein in their respective entireties.

BIBLIOGRAPHY

See, for example, Holoman, T. R. P., Elberson, M. A., Cutter, L., May, H. D., and Sowers, K. R., 1998, Characterization of a defined 2,3,5,6-tetrachlorobiphenyl ortho-dechlorinating microbial community by comparative sequence analysis of genes coding for 16S rDNA, Appl. Environ. Microbiol., 64:3359–3367.

Presentation: Acetate-Dependent ortho PCB Dechlorination, Joint Meeting of the Southeastern Branches, American Society for Microbiology, Oct. 28–30, 1999, Jekyll Island, Ga.

Berkaw, M., Sowers, K. R. and May, H. D., 1996, Anaerobic ortho-dechlorination of polychlorinated biphenyls by estuarine sediments from Baltimore Harbor, Appl. Environ. Microbiol., 62: 2534–2539

Wu, Q., Sowers, K. R. and May, H. D., Microbial reductive dechlorination of Aroclor 1260 in anaerobic slurries of estuarine sediments, Appl. Environ. Microbiol. 64:1052–1058

Cutter, L., Sowers, K. R. and May, H. D., May, 1998, Ortho-dechlorination of 2,3,5,6-chlorinated biphenyl by estuarine microbial populations in sediment-free enrichment cultures, Appl. Environ. Microbiol., 64:2966–2969

U.S. Pat. No. 5,484,729 issued Jan. 16, 1996 to DeWeerd and Bedard

U.S. Pat. No. 5,227,069 issued July, 1993 to VanDort et al.

U.S. Pat. No. 5,635,393 issued Jun. 3, 1997 to Bhatnagar et al.

Clark et al., 1979, Applied and Environmental Microbiology, Vol. 37, No. 4

Bedard, D. L. and Quensen, III, J. F., 1995, Microbial reductive dechlorination of polychlorinated biphenyls, p. 127–216, in Young, L. Y. and Cerniglia, C. (eds.), Microbial transformation and degradation of toxic organic chemicals, John Wiley & Sons, Inc., New York.

Cole, J. R., Cascarelli, A. L., Mohn, W. W., and Tiedje, J. M., 1994, Isolation and characterization of a novel bacterium growing via reductive dechlorination of 2-chlorophenol, Appl. Environ. Microbiol., 60(10), 3536–3542.

Cutter, L., Sowers, K. R. and May, H. D., May, 1998, Microbial dechlorination of 2,3,5,6-tetrachlorobiphenyl under anaerobic conditions in the absence of soil or sediment, Appl. Environ. Microbiol., 64(8):2966–2969.

DeWeerd, K. A., Concannon, F. and Suflita, J. M. (1991), Relationship between hydrogen consumption, dehalogenation, and the reduction of sulfur oxyanions by *Desulfomonile tiedjei*, Appl. Environ. Microbiol., 57 (7): 1929–1934.

Freedman, D. L., and Cossett, J. M., 1989, "Biological reductive dechlorination of tetrachloroethylene and trichloroethylene under methanogenic conditions, Appl. Environ. Microbiol. 55:2144–2151.

May, H. D., Cutter, L. A., Watts, J. E. M. and Sowers, K. R, Molecular Identification of an Anaerobic Microorganism Whose Growth is Linked to PCB Dechlorination, presented at The 17th Annual International Conference on Contaminated Soils, Sediments and Water, October 15–19, 2000, University of Massachusetts at Amherst.

Maymo-Gatell, X., Chien, Y. T., Gossett, J. M., and Zinder, S. H., 1997, Isolation of a bacterium that reductively dechlorinates tetrachloroethene to ethane, Science, 276:1568–1571.

Middeldorp, P. J. M., DeWolf, A., Zehnder, J. B. and Schraa, G., 1997, Enrichment and properties of a 1,2,4-trichlorobenzene-dechlorinating methanogenic microbial consortium, Appl. Environ. Mircrobiol., 63(4): 1225–1229.

Morris, P. J., Mohn, W. W., Quensen, III, J. F., Tiedje, J. M. and Boyd, S. A., 1992, Establishment of a polychlorinated biphenyl-degrading enrichment culture with predominantly meta dechlorination, Appl. Environ. Microbiol., 58(9) :3088–3094.

Nies, L. and Vogel, T. M., 1990, Effects of organic substrates on dechlorination of Aroclor 1242 in anaerobic sediments, Appl. Environ. Microbiol., 56:2612–2617.

Nies, L. and Vogel, T. M., 1991, Identification of the proton source for the microbial reductive dechlorination of 2,3,4,5,6-pentachlorobiphenyl, Appl. Environ. Microbiol., 57(9): 2771–2774.

Pulliam-Holoman, T. R. P., M. A. Elberson, L. Cutter, H. D. May, and K. R. Sowers, 1998, Characterization of a defined 2,3,5,6-tetrachlorobiphenyl-ortho-dechlorinating microbial community by comparative sequence analysis of genes coding for 16S rDNA. Appl. Environ. Microbiol., 64:3359–3367.

Figure 28:
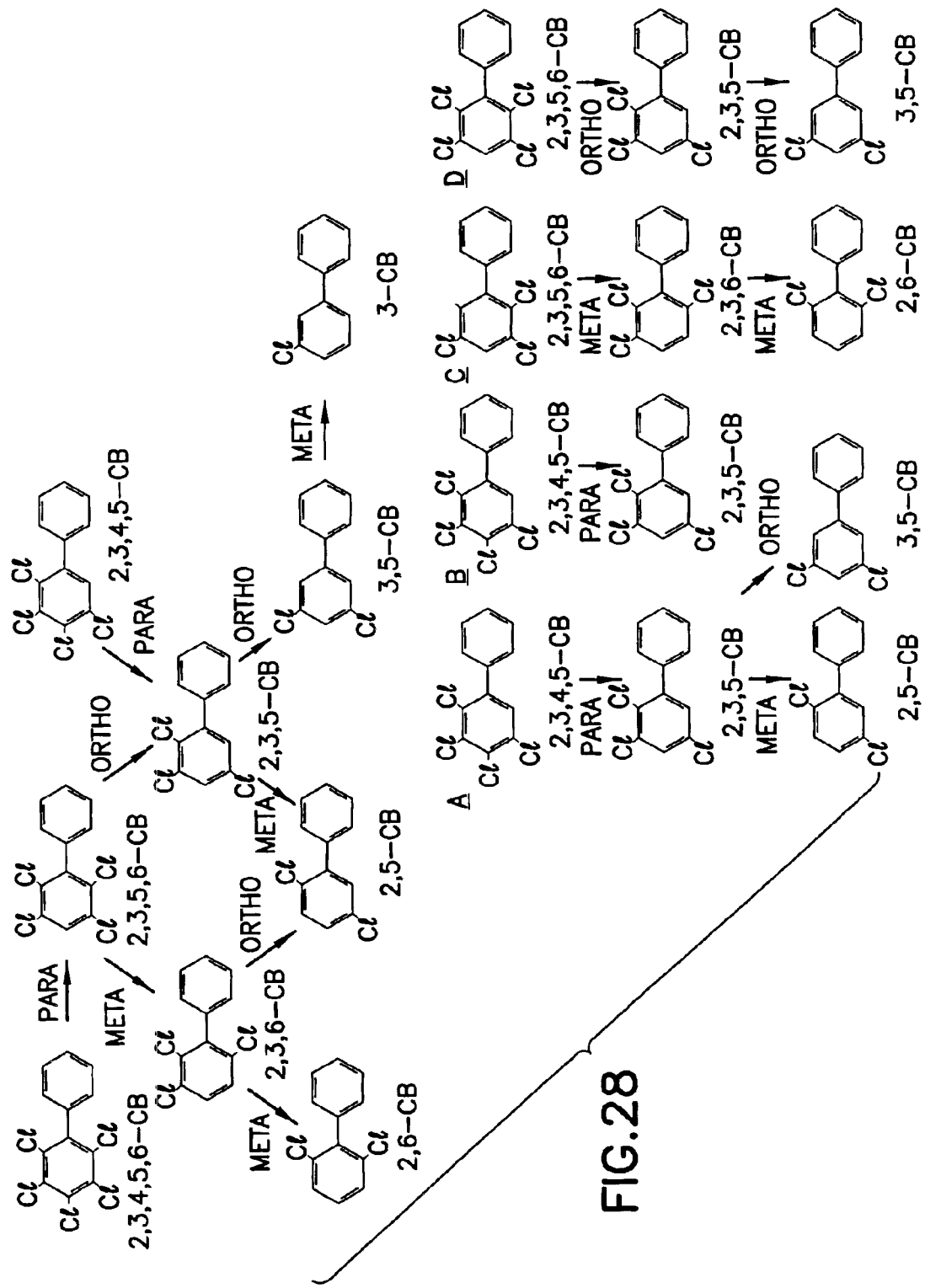
FIG. 28 is a schematic representation of various PCB dechlorination pathways.

FIG. 28 is a schematic representation of various PCB dechlorinating pathways. The schematic representation evidences a variety of dechlorination pathways for corresponding highly chlorinated PCBs that have been demonstrated with anaerobic bacteria of the invention variously having the sequences shown in FIGS. 21–23. The chlorinated species A, B, C and D are representative of PCB dechlorination pathways that have been demonstrated for Baltimore Harbor sediments containing such highly chlorinated species.

While the invention has been described herein with reference to various illustrative features, aspects, and embodiments, it will be appreciated that the utility of the invention is not thus limited, but rather extends to and encompasses other variations, modifications and other embodiments, as will readily suggest themselves to those of ordinary skill in the art. Accordingly, the invention is to be broadly interpreted and construed as including such other variations, modifications and other embodiments, within the spriit and scope of the invention as hereinafter claimed.

What is claimed is:

1. An isolated bioremediative microorganism for PCB ortho dechlorination comprising a 16S ribosomal subunit nucleic acid sequence selected from the group consisting of:
   (a) a nucleic acid sequence that has more than 95% identity to a nucleic acid sequence of SEQ ID NO 1; and
   (b) a nucleic acid sequence fully complementary to a nucleic acid of (a); and
wherein the isolated bioremediative microorganism anaerobically dechlorinates chlorinated biphenyls.

2. An isolated bioremediative microorganism comprising a 16S ribosomal subunit nucleic acid sequence consisting of SEQ ID NO 1.

3. The isolated bioremediative microorganism of claim 2, in combination with an additive for enhancing the dechlorination efficacy.

4. A method for dechlorinating chlorinated biphenyls, comprising introducing at least one microorganism as in claim 1 to a system comprising chlorinated biphenyls, and providing growth conditions for said microorganism such that at least one chlorine molecule per chlorinated biphenyl molecule is removed from said chlorinated biphenyl.

5. The method of claim 4, wherein said growth conditions include the presence of an agent for enhancing the dechlorination efficacy.

6. The method of claim 5, wherein said agent is present as an additive.

7. An isolated bioremediative microorganism comprising a 16S ribosomal subunit nucleic acid sequence selected from the group consisting of:
   (a) a nucleic acid sequence that has more than 98% identity to a nucleic acid sequence consisting of SEQ ID NO 1; and
   (b) a nucleic acid sequence fully complementary to a nucleic acid of (a), and wherein the isolated bioremediative microorganism anaerobically dechlorinates chlorinated biphenyls.

8. An isolated bioremediative microorganism comprising SEQ ID NO 1.

9. The bioremediative microorganism of claim 8, in combination with a dechlorination efficacy-enhancing agent, selected from the group consisting of hydrogen, acetate, formate and fumarate.

10. A method for dechlorinating chlorinated biphenyl, comprising contacting said chlorinated biphenyl with at least one microorganism comprising a 16S ribosomal subunit nucleic acid sequence selected from the group consisting of:
   (a) a nucleic acid sequence that has more than 95% identity to a nucleic acid sequence consisting of SEQ ID NO 1; and
   (b) a nucleic acid sequence complementary to a nucleic acid of (a); and wherein the isolated bioremediative microorganism anaerobically dechlorinates chlorinated biphenyls,
for sufficient time and under sufficient conditions to at least partially dechlorinate said chlorinated biphenyl.

11. The method of claim 10, wherein at least one chlorine molecule per chlorinated biphenyl molecule is removed during said contacting.

12. The method of claim 10, wherein said contacting comprises dechlorination of a flanked chlorine substituent of the chlorinated biphenyl.

13. A method of determining the bioremediative potential of a chlorinated biphenyl-containing site, comprising contacting a nucleic acid molecule comprising a nucleic acid sequence selected from the group consisting of:
   (a) a nucleic acid sequence that has more than 95% identity to a nucleic acid sequence consisting of SEQ ID NO 1; and
   (b) a nucleic acid sequence fully complementary to a nucleic acid of (a)
with a nucleic acid molecule from said site under high stringency hybridization conditions, whereby occurrence of hybridization is indicative of a positive bioremediation potential of said site.

14. The method of claim 13, further comprising subjecting said site to bioremediation treatment subsequent to said occurrence of hybridization.

15. The method of claim 14, wherein said bioremediation treatment includes microbial dechlorination of PCBs at said site.

16. The method of claim 14, wherein said contacting of said nucleic acid sequences is carried out at intervals during said bioremediation treatment, to determine progress or a conclusion thereof.

17. A method for monitoring a chlorinated biphenyl-containing site, comprising conducting serial observations using a method as in claim 14.

18. A PCB-degradative composition comprising:
(i) microorganism comprising a 16S ribosomal subunit nucleic acid sequence selected from the group consisting of:
   a) a nucleic acid sequence that has more than 95% identity to a nucleic acid sequence consisting of SEQ ID NO 1; and
   b) a nucleic acid sequence fully complementary to a nucleic acid of (a); and wherein the microorganism anaerobically dechlorinates chlorinated biphenyls, and
(ii) a PCB degradation-enhancing agent for said microorganism.

19. The composition of claim 18, wherein said PCB degradation-enhancing agent for said microorganism, comprises a component selected from the group consisting of hydrogen, acetate, formate and fumarate.

20. A composition for broad spectrum dechlorination of a multi-congener mixture of chlorinated biphenyls, said composition comprising a non-naturally occurring consortium of dechlorinatingly effective microbial species, wherein said consortium of dechlorinatingly effective microbial species comprises a nucleic acid sequence that has more than 95% identity to a nucleic acid sequence consisting of SEQ ID NO 1 and wherein the microbial species anaerobically dechlorinates chlorinated biphenyls.

21. The composition of claim 20, wherein said consortium of dechlorinatingly effective microbial species comprises dechlorinatingly effective anaerobic microbial species.

22. The composition of claim 20, wherein said consortium of dechlorinatingly effective microbial species comprises dechlorinatingly effective anaerobic microbial species in mixture with dechlorinatingly effective aerobic microbial species.

23. A method of bioremediation comprising overlyingly capping a PCB-containing material with a sedimentary composition including a composition as in claim 20.

24. A composition for broad spectrum dechlorination of a multi-congener mixture of chlorinated biphenyls, said composition comprising a non-naturally occurring consortium of dechlorinatingly effective microbial species, and at least one growth additive for at least one microbial species in said consortium, and wherein said consortium of dechlorinatingly effective microbial species comprises a nucleic acid sequence that has more than 98% identity to a nucleic acid sequence consisting of SEQ ID NO 1 and wherein the microbial species anaerobically dechlorinates chlorinated biphenyls.

25. The composition of claim 24, wherein said consortium of dechlorinatingly effective microbial species comprises dechlorinatingly effective anaerobic microbial species in mixture with dechlorinatingly effective aerobic microbial species.

26. An isolated bioremediative microorganism for PCB ortho dechlorination comprising a 16S ribosomal subunit nucleic acid sequence selected from the group consisting of:
   (a) a nucleic acid sequence that has more than 95% identity to a nucleic acid sequence of SEQ ID NO 1, and hybridizes therewith under high stringency conditions; and
   (b) a nucleic acid sequence fully complementary to a nucleic acid of (a) and hybridizes therewith under high stringency conditions; and
wherein the isolated bioremediative microorganism anaerobically dechlorinates chlorinated biphenyls.

* * * * *

UNITED STATES PATENT AND TRADEMARK OFFICE
CERTIFICATE OF CORRECTION

PATENT NO.    : 6,946,248 B2
DATED         : September 20, 2005
INVENTOR(S)   : Kevin R. Sowers et al.

It is certified that error appears in the above-identified patent and that said Letters Patent is hereby corrected as shown below:

Title page,
Item [73], Assignees, "University of Maryland, Baltimore, MD (US); Biotechnology Institute" should be -- University of Maryland Biotechnology Institute, Baltimore, MD (US); --.

Column 13,
Line 22, "the DOGE gel" should be -- the DGGE gel --.
Line 59, "1000X" should be -- 10000X --.

Column 16,
Line 9, "5 µM" should be -- 5 mM --.

Column 19,
Line 42, "(SFQ ID NO." should be -- (SEQ ID NO. --.
Line 44, "Primer 3 14F" should be -- Primer 314F --.

Column 33,
Lines 28-29, "a nucleic acid sequence that has more than 95% identity to a nucleic acid sequence of SEQ ID NO 1" should be -- a nucleic acid sequence consisting of SEQ ID NO 1 --.
Lines 39-40, "enhancing the dechlorination efficiency" should be -- enhancing dechlorination efficiency --.
Lines 55-56, "a nucleic acid sequence that has more than 98% identity to a nucleic acid sequence consisting of SEQ ID NO 1" should be -- a nucleic acid sequence consisting of SEQ ID NO 1 --.

Column 34,
Lines 28-29, "a nucleic acid sequence that has more than 95% identity to a nucleic acid sequence consisting of SEQ ID NO 1" should be -- a nucleic acid sequence consisting of SEQ ID NO 1 --.
Lines 31-33, "a nucleic acid sequence complementary to a nucleic acid of (a); and wherein the isolated bioremediative microorganism" should be -- a nucleic acid sequence fully complementary to a nucleic acid of (a); and wherein the isolated microorganism --.
Lines 47-49, "a nucleic acid sequence that has more than 95% identity to a nucleic acid sequence consisting of SEQ ID NO 1" should be -- a nucleic acid sequence consisting of SEQ ID NO 1 --.

UNITED STATES PATENT AND TRADEMARK OFFICE
CERTIFICATE OF CORRECTION

PATENT NO. : 6,946,248 B2
DATED : September 20, 2005
INVENTOR(S) : Kevin R. Sowers et al.

It is certified that error appears in the above-identified patent and that said Letters Patent is hereby corrected as shown below:

Column 35,
Lines 5-7, "a nucleic acid sequence that has more than 95% identity to a nucleic acid sequence consisting of SEQ ID NO 1" should be -- a nucleic acid sequence consisting of SEQ ID NO 1 --.
Lines 23-25, "comprises a nucleic acid sequence that has more than 95% identity to a nucleic acid sequence consisting of SEQ ID NO 1" should be -- comprises a microbial species comprising a nucleic acid sequence consisting of SEQ ID NO 1 --.
Lines 28-29, "comprises dechlorinatingly effective anaerobic microbial species" should be -- comprises naturally occurring dechlorinatingly effective anaerobic microbial species --.

Column 36,
Lines 10-12, "comprises a nucleic acid sequence that has more than 98% identity to a nucleic acid sequence consisting of SEQ ID NO 1" should be -- comprises a microbial species comprising a nucleic acid sequence consisting of SEQ ID NO 1 --.
Lines 20-32, "26. An isolated bioremediative microorganism for PCB ortho dechlorination comprising a 16S ribosomal subunit nucleic acid sequence selected from the group consisting of: (a) a nucleic acid sequence that has more than 95% identity to a nucleic acid sequence of SEQ ID NO 1, and hybridizes therewith under high stringency conditions; and (b) a nucleic acid sequence fully complementary to a nucleic acid of (a) and hybridizes therewith under high stringency conditions; and wherein the isolated bioremediative microorganism anaerobically dechlorinates chlorinated biphenyls" should be deleted.

Signed and Sealed this

Fourth Day of April, 2006

JON W. DUDAS
*Director of the United States Patent and Trademark Office*

SEQUENCE LISTING

```
<160> NUMBER OF SEQ ID NOS: 9

<210> SEQ ID NO 1
<211> LENGTH: 1359
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (548)..(548)
<223> OTHER INFORMATION: n = any one of a, c, t, and g.

<400> SEQUENCE: 1
gagtttgatc ctggctcagg atgaacgcta gcggcgtgct ttatgcatgc aagtcgaacg     60
```

```
gttttttgagt cttcggactt aaaaatagtg gcaaacgggt gagtaacacg taggtaactt      120 accctaagt  ttgggataac tccgggaaac cggggctaat accggatgtg gtgagcgggt       180
aatgcctgtt cactaaagcc ttcggcgct  tggggaaagg cctgcgtccg attagcttgt       240
tggtggggta atggctcacc aaggctatga tcggtagctg gcctgagagg acggtcagcc       300
acactgggac tgagacacgg cccagactcc tacgggaggc agcagcaagg aattttgggc       360
aatgggcgaa agcctgaccc agcaacgccg cgtgggggat gaaggccctc gggttgtaaa       420
ccccttttcc cagggaagaa tgatgacggt acctggggaa taagcccggg ctaactacgt       480
gccagcagcc gcgtaatac  gtaggggggca agcgttatcc ggatttactg ggcgtaaaga      540
ggacgtangc ggcttttcaa gtcggatgtg aaatttcccg gctcaaccgg gatgagtcat       600
tcgatactgt tgggctagag gatagcaggg ggagacggaa ttcccggtgt agtggtggaa       660
tacgtagata ccgggaggaa caccagaggc gaaggcggtc tccaaggcta tttctgacgc       720
tgaggtccga aagcgtgggt agcaaacaga cttagatact ctggtagtcc acgctgtaaa       780
cgatggacac taggtatagg gagcatcgac cctctttgtg ccgaagctaa cgctttaagt       840
gtcccgcctg gggactacgg ccgcaaggct aaaactcaaa ggaattgacg ggggcccgca       900
caagcagcgg agcgtgtggt ttaattcgat gcaacgcgaa gaaccttacc aaggcttgac       960
atgtcggaag tagtgaaccg aaaggggaac gacccgttaa atcgggagcc gtcacaggtg      1020
ctgcatggct gtcgtcagct cgtgccgtga ggtgtatggt taagtcctgc aacgagcgca      1080
accctcgtcg ctagttgaat tctctagcga gaccgccctg caaaacgggg aggaaggtgg      1140
ggatgacgtc aagtcagcat ggcccttatg ccttgggcta cacacacgct acaatgggtg      1200
gtacagcagg tagcaatagg taacctggag ctaatcccta aaaccatcct cagttcggat      1260
tgtaggctga aactcgcctg catgaagctg gagttgctag taaacgcgta tcagcacggc      1320
gcgttgaata cgttttcggg ccttgtacac accgcccgt                             1359
```

<210> SEQ ID NO 2
<211> LENGTH: 336
<212> TYPE: DNA
<213> ORGANISM: Artificial Sequence
<220> FEATURE:
<223> OTHER INFORMATION: Synthetic Construct

<400> SEQUENCE: 2

```
atggctgtgg tcagctcgtg ccgtgaggtg tttggttaag tcctgcaacg agcgcaaccc       60
tcatcgttag ttgttttctc tagcgagact gccctgcaaa acggggagga aggtggggat      120
gacgtcaagt cagcatggcc cttatgccta gggctacaca cacgctacaa tgggtggtac      180
aattggttgc aatggagcaa tccggagcca atccgtaaag ccactctcag ttcggattac      240
aggctgaaac tcgcctgtat gaagttggag ttgctagtaa ccgcaggtca gcatactgcg      300
gtgaatacgt tctcgggcct tgtacacacc gcccgt                                336
```

<210> SEQ ID NO 3
<211> LENGTH: 880
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (66)..(66)
<223> OTHER INFORMATION: n = any one of a, c, t, and g.

<400> SEQUENCE: 3

```
cagccgccgc ggtaatacgt aggggggcaag cgttatccgg atttactggg cgtaaagagg      60
acgtanggcg gctttttcaag tcggatgtga aatttcccgg ctcaaccggg atgagtcatt     120
cgatactgtt gggctagagg atagcagggg gagacggaat tcccggtgta gtggtggaat     180
acgtagatac cggaggaac accagaggcg aaggcggtct ccaaggctat ttctgacgct      240
gaggtccgaa agcgtgggta gcaaacagac ttagatactc tggtagtcca cgctgtaaac     300
gatggacact aggtataggg agcatcgacc ctctttgtgc cgaagctaac gctttaagtg     360
tcccgcctgg ggactacggc cgcaaggcta aaactcaaag gaattgacgg gggcccgcac     420
aagcagcgga gcgtgtggtt taattcgatg caacgcgaag aaccttacca aggcttgaca     480
tgtcggaagt agtgaaccga aaggggaacg acccggttaa atcgggagcc gtcacaggtg     540
ctgcatggct gtcgtcagct cgtgccgtga ggtgtatggt taagtcctgc aacgagcgca     600
accctcgtcg ctagttgaat tctctagcga gaccgccctg caaaacgggg aggaaggtgg     660
ggatgacgtc aagtcagcat ggcccttatg ccttgggcta cacacacgct acaatgggtg     720
gtacagcagg tagcaataggg gtaacctgga gctaatccct aaaaccatcc tcagttcgga     780
ttgtaggctg aaactcgcct gcatgaagct ggagttgcta gtaaacgcgt atcagcacgg     840
cgcgttgaat acgttttcgg gccttgtaca caccgcccgt                          880
```

```
<210> SEQ ID NO 4
<211> LENGTH: 16
<212> TYPE: DNA
<213> ORGANISM: Artificial Sequence
<220> FEATURE:
<223> OTHER INFORMATION: Synthetic Construct

<400> SEQUENCE: 4
atggctgtcg tcagct                                                     16

<210> SEQ ID NO 5
<211> LENGTH: 15
<212> TYPE: DNA
<213> ORGANISM: Artificial Sequence
<220> FEATURE:
<223> OTHER INFORMATION: Synthetic Construct

<400> SEQUENCE: 5
acgggcggtg tgtac                                                      15

<210> SEQ ID NO 6
<211> LENGTH: 18
<212> TYPE: DNA
<213> ORGANISM: Artificial Sequence
<220> FEATURE:
<223> OTHER INFORMATION: Synthetic Construct

<400> SEQUENCE: 6
cagccgccgc ggtaattc                                                   18

<210> SEQ ID NO 7
<211> LENGTH: 15
<212> TYPE: DNA
<213> ORGANISM: Artificial Sequence
<220> FEATURE:
<223> OTHER INFORMATION: Synthetic Construct

<400> SEQUENCE: 7
acgggcggtg tgtgc                                                      15
```

```
<210> SEQ ID NO 8
<211> LENGTH: 17
<212> TYPE: DNA
<213> ORGANISM: Artificial Sequence
<220> FEATURE:
<223> OTHER INFORMATION: Synthetic Construct

<400> SEQUENCE: 8
cctacgggag gcagcag                                                  17

<210> SEQ ID NO 9
<211> LENGTH: 17
<212> TYPE: DNA
<213> ORGANISM: Artificial Sequence
<220> FEATURE:
<223> OTHER INFORMATION: Synthetic Construct

<400> SEQUENCE: 9
attaccgcgg ctgctgg                                                  17
```